(12) United States Patent
Millar et al.

(10) Patent No.: US 10,385,003 B2
(45) Date of Patent: Aug. 20, 2019

(54) OPHTHALMIC FORMULATION

(71) Applicants: Thomas Millar, New South Wales (AU); Burkhardt Schuett, New South Wales (AU)

(72) Inventors: Thomas Millar, New South Wales (AU); Burkhardt Schuett, New South Wales (AU)

( * ) Notice: Subject to any disclaimer, the term of this patent is extended or adjusted under 35 U.S.C. 154(b) by 0 days.

(21) Appl. No.: 14/367,836

(22) PCT Filed: Dec. 21, 2012

(86) PCT No.: PCT/AU2012/001595
§ 371 (c)(1),
(2) Date: Jun. 20, 2014

(87) PCT Pub. No.: WO2013/091020
PCT Pub. Date: Jun. 27, 2013

(65) Prior Publication Data
US 2014/0377335 A1 Dec. 25, 2014

(30) Foreign Application Priority Data
Dec. 23, 2011 (AU) .............................. 2011905421

(51) Int. Cl.
| | |
|---|---|
| *A61K 9/00* | (2006.01) |
| *A61K 9/06* | (2006.01) |
| *A61K 9/08* | (2006.01) |
| *A61K 31/23* | (2006.01) |
| *A61K 47/14* | (2017.01) |
| *A61K 47/38* | (2006.01) |
| *A61K 9/107* | (2006.01) |
| *C07C 67/14* | (2006.01) |
| *C07C 69/22* | (2006.01) |
| *C07C 69/26* | (2006.01) |
| *C07C 69/58* | (2006.01) |
| *A61K 31/231* | (2006.01) |
| *A61K 31/232* | (2006.01) |
| *C07C 69/533* | (2006.01) |
| *C07C 69/587* | (2006.01) |

(52) U.S. Cl.
CPC .......... *C07C 69/533* (2013.01); *A61K 9/0048* (2013.01); *A61K 9/0051* (2013.01); *A61K 9/06* (2013.01); *A61K 9/08* (2013.01); *A61K 9/107* (2013.01); *A61K 31/23* (2013.01); *A61K 31/231* (2013.01); *A61K 31/232* (2013.01); *A61K 47/14* (2013.01); *A61K 47/38* (2013.01); *C07C 67/14* (2013.01); *C07C 69/22* (2013.01); *C07C 69/26* (2013.01); *C07C 69/58* (2013.01); *C07C 69/587* (2013.01)

(58) Field of Classification Search
None
See application file for complete search history.

(56) References Cited

U.S. PATENT DOCUMENTS

2008/0312194 A1* 12/2008 Ousler et al. ............... 514/152
2011/0124725 A1*  5/2011 Maskin ....................... 514/529
2014/0377335 A1   12/2014 Millar et al.

FOREIGN PATENT DOCUMENTS

| AU | 2012318266 | 7/2013 |
| FR | 2855047 | 11/2004 |
| WO | 2010-106571 | 9/2010 |
| WO | 2013091020 | 6/2013 |

OTHER PUBLICATIONS

Butovich I, Human tear film and meibum. Very long chain wax esters and (O-acyl)-omega-hydroxy fatty acids of meibum, J Lipid Res, 2009, 50, 2471-2485.*
Lam S, Meibum lipid composition in Asians with disease, PLOS One, 6(10), 1-13, 2011.*
Butovich, Igor et al., Human Tear Film and Meibum. Very Long Chain Wax Esters and (O-acyl)-omega-hydroxy Fatty Acids of Meibum, J. Lipid Research 2009, 50: 2471-2485.
Wohlman, Alan, Meadowestolide and Meadowlactone: Unique Materials for Skin Care and Pigmented Products, Surfactants in Personal Care Products and Decorative Cosmetics, 3rd Edition, 2007, 357-361.
International Search Report & the Written Opinion dated Jan. 25, 2013 for PCT/AU2012/001595 filed on Dec. 2012 in the name of University of Western Sydney et al.
Extended European Search Report & Opinion dated Sep. 18, 2015 for EP 12860686.0 filed on Jul. 18, 2014 in the name of University of Western Sydney.
Lam, Sin Man et al., Meibum Lipid Composition in Asians with Dry Eye Disease, PLoS One 2011, 6: e24339-1-e24339-13 (6).
Ranu, B.C., et al., Highly efficent acylation of alcohols, amines and thiols under solvent-free and catalyst-free conditions, Green Chemistry, 2003, 44-46, 5.

* cited by examiner

*Primary Examiner* — Celeste A Roney
(74) *Attorney, Agent, or Firm* — Lorenz Siddiqi

(57) ABSTRACT

Disclosed herein is an ophthalmic formulation comprising a compound of formula (I):

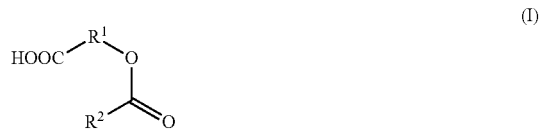

(I)

wherein
R$^1$ is a linear or branched C$_9$-C$_{33}$ alkyl or a linear or branched C$_9$-C$_{33}$ alkenyl with 1 to 4 double bonds;
R$^2$ is a linear or branched C$_9$-C$_{19}$ alkyl or a linear or branched C$_9$-C$_{19}$ alkenyl with 1 to 4 double bonds;
and an ophthalmologically acceptable carrier.

19 Claims, 6 Drawing Sheets

OPHTHALMIC FORMULATION

CROSS REFERENCE TO RELATED APPLICATIONS

This is a national stage application under 35 U.S.C. § 371 of International Application No. PCT/AU2012/001595, filed Dec. 21, 2012, which claims the benefit of Australian Patent Application No. 2011905421, filed Dec. 23, 2011, the disclosure of each of which is hereby incorporated by reference in its entirety.

TECHNICAL FIELD

The present invention relates to ophthalmic formulations and to methods for treating dry eye.

BACKGROUND ART

Ocular comfort requires the maintenance of a continuous film known as preocular tear film or lachrymal film on the ocular surface, and proper function of the lids to regularly re-spread the tear film before it breaks down.

Dry eye, also known as dysfunctional tear syndrome, is one of the most frequently encountered ocular morbidities and one of the most common disease conditions diagnosed by eye care practitioners. Dry eye has a wide range of signs, symptoms and underlying etiologies. Dry eye is a multifactorial disease of the tears and ocular surface that results in symptoms of discomfort, visual disturbance, and tear film instability with potential damage to the ocular surface. It is accompanied by increased osmolarity of the tear film and inflammation of the ocular surface. Dry eye can be caused by a multitude of causes, such as neural loop dysfunction, mucin deficiency (e.g. goblet cell deficiency or goblet cell dysfunction), primary or secondary inflammation, meibomitis, and lachrymal gland dysfunction as a result of, for example, autoimmune disease (e.g. Sjogren's disease), dysfunctional innervation and damage to the ocular glands.

Excess evaporation of the tear film, usually caused by meibomian gland dysfunction or related lid disorder, is a major underlying feature of dry eye. As a result, symptoms include unpleasantness in the eyes, itchiness, redness, excessive tearing, discomfort after periods of eye strain, inflammation, and damage to the ocular surface.

Management of dry eye has conventionally been achieved by use of lubricant eye drops to provide temporary symptomatic relief, surgical procedures such as punctal plugs, or, more recently, pharmacological therapy for underlying inflammation with cyclosporine A. Other pharmacological agents are currently in development, but initial therapy for most new patients with dry eye consists of artificial tear formulations. There are a number of different artificial tear formulations for medicinal purposes currently on the market. None of these formulations has the physico-chemical properties of real tears.

It would be advantageous to provide an ophthalmic formulation which more closely mimics the physico-chemical properties of tear lipids.

DISCLOSURE OF INVENTION

The present invention provides the following items 1 to 24:

1. An ophthalmic formulation comprising a compound of formula (I):

wherein
$R^1$ is a linear or branched $C_9$-$C_{33}$ alkyl or a linear or branched $C_9$-$C_{33}$ alkenyl with 1 to 4 double bonds;
$R^2$ is a linear or branched $C_9$-$C_{19}$ alkyl or a linear or branched $C_9$-$C_{19}$ alkenyl with 1 to 4 double bonds;
and an ophthalmologically acceptable carrier.

2. An ophthalmic formulation according to item 1, wherein HOOC—$R^1$— is selected from the group consisting of: capryl (C10:0), lauryl (C12:0), myristyl (C14:0), palmityl (C16:0), stearyl (C18:0), oleoyl (C18:1), linoleoyl (ω6) (C18:2), and linoleoyl (ω3) (C18:3).

3. An ophthalmic formulation according to item 1 or 2, wherein $R^2$ is linear or branched $C_{17}$ alkyl or linear or branched $C_{17}$ alkenyl with 1 or 2 double bonds.

4. An ophthalmic formulation according to item 1 or 2, wherein $R^2$ is linear or branched $C_{19}$ alkenyl with 4 double bonds.

5. An ophthalmic formulation according to any one of items 1 to 4, wherein the compound of formula (I) is selected from the group consisting of:

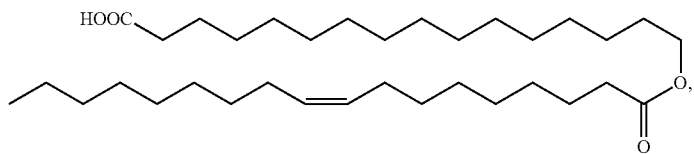

(O-oleoyl)-16-hydroxypalmitic acid (C16:0-C18:1)

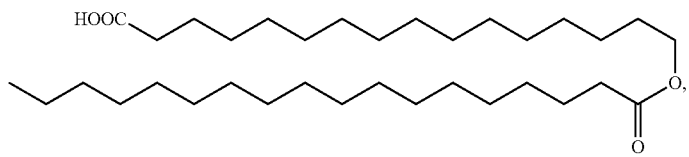

(O-stearyl)-16-hydroxypalmitic acid (C16:0-C18:0)

-continued

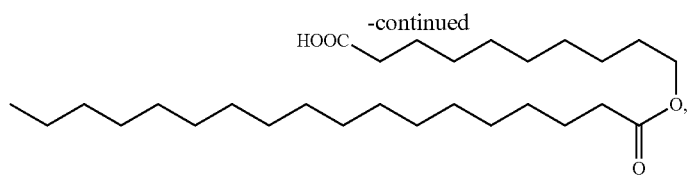

(O-stearyl)-10-hydroxycaprinic acid (C10:0-C18:0)

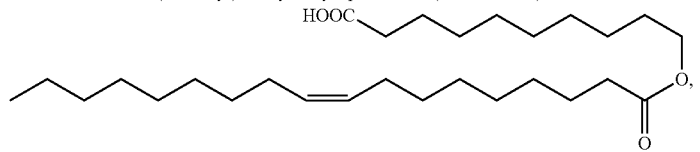

(O-oleoyl)-10-hydroxycaprinic acid (C10:0-C18:1)

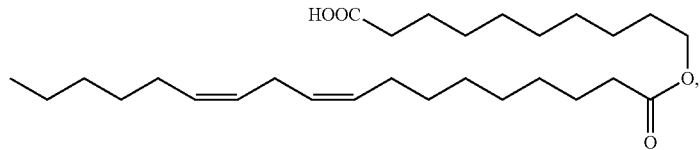

(O-linoleoyl)-10-hydroxycaprinic acid (C10:0-C18:2)

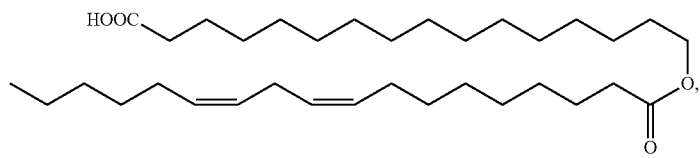

(O-linoleoyl)-16-hydroxypalmitic acid (C16:0-C18:2)

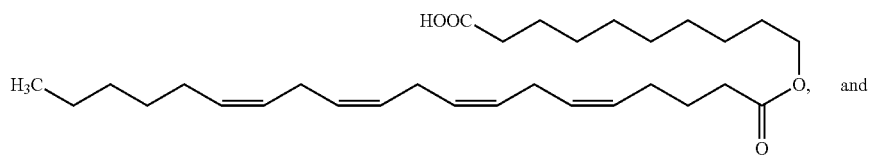

(O-arachidonyl)-10-hydroxycaprinic acid (C10:0-C20:4)

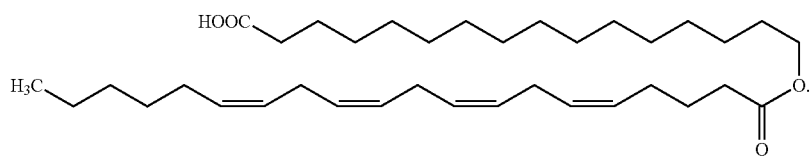

(O-arachidonyl)-16-hydroxypalmitic acid (C16:0-C20:4)

6. An ophthalmic formulation according to item 1, wherein the compound of formula (I) is (O-oleoyl)-16-hydroxypalmitic acid.

7. An ophthalmic formulation according to item 1, wherein the ophthalmologically acceptable carrier is, or comprises, water.

8. An ophthalmic formulation according to any one of items 1 to 7, wherein the ophthalmic formulation further comprises an ophthalmologically acceptable excipient.

9. An ophthalmic formulation according to item 8, wherein the ophthalmologically acceptable excipient is selected from the group consisting of demulcents, emollients, hypertonicity agents, preservatives, buffers and pH adjusting agents.

10. An ophthalmic formulation according to any one of items 1 to 9, wherein the ophthalmic formulation is an oil-in-water emulsion.

11. An ophthalmic formulation according to any one of items 1 to 10, wherein the ophthalmic formulation comprises liposomes.

12. An ophthalmic formulation comprising a compound of formula (I) as defined in item 1, water, and an emulsifying agent.

13. An ophthalmic formulation comprising a compound of formula (I) as defined in item 1, water, and one or more ophthalmologically acceptable excipients selected from the group consisting of polyethylene glycol, propylene glycol, glycerin, polyvinyl alcohol, povidone, polysorbate 80, hydroxypropyl methylcellulose, carmellose, carbomer 980, sodium hyaluronate and dextran.

14. An ophthalmic formulation according to any one of items 1 to 13, further comprising an active pharmaceutical ingredient for treating a condition or disease of the eye.

15. A method for the treatment of dry eye comprising topically administering to the eye of a subject in need thereof a therapeutically effective amount of an ophthalmic formulation according to any one of items 1 to 14.

16. Use of a compound of formula (I) as defined in item 1 in the manufacture of an ophthalmic formulation for the treatment of dry eye.

17. A compound of the following formula:

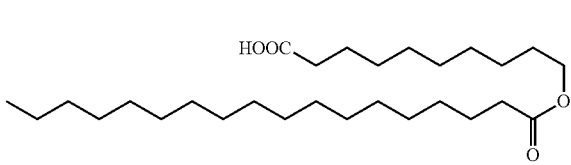

(O-stearyl)-10-hydroxycaprinic acid (C10:0-C18:0)

18. A compound of the following formula:

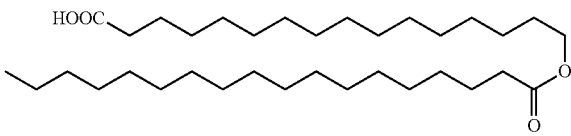

(O-stearyl)-16-hydroxypalmitic acid (C16:0-C18:0)

19. A compound of the following formula:

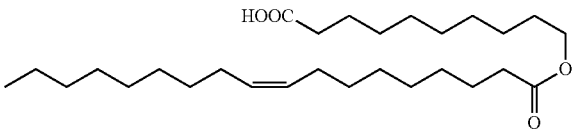

(O-oleoyl)-10-hydroxycaprinic acid (C10:0-C18:1)

20. A compound of the following formula:

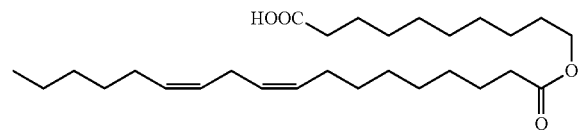

(O-linoleoyl)-10-hydroxycaprinic acid (C10:0-C18:2)

21. A compound of the following formula:

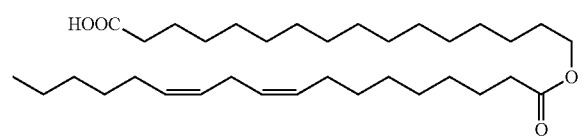

(O-linoleoyl)-16-hydroxypalmitic acid (C16:0-C18:2)

22. A compound of the following formula:

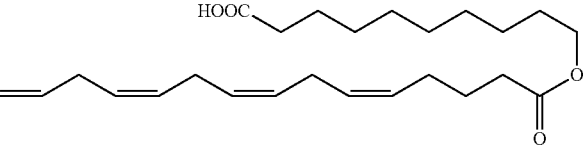

(O-arachidonyl)-10-hydroxycaprinic acid (C10:0-C20:4)

23. A compound of the following formula:

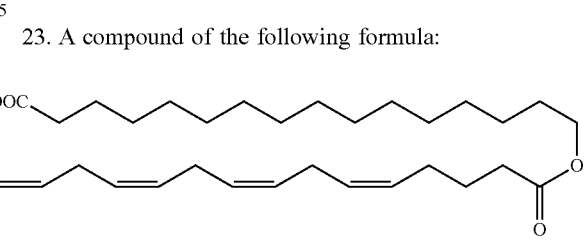

(O-arachidonyl)-16-hydroxypalmitic acid (C16:0-C20:4)

24. A method for the preparation of a compound of any one of items 17 to 23 comprising the following step:
mixing a compound of the formula HOOC—R$^a$—OH wherein R$^a$ is —(CH$_2$)$_9$— or —(CH$_2$)$_{15}$—,
with an acid chloride selected from stearoyl chloride, oleoyl chloride, linoleoyl chloride and arachinoyl chloride,
in the absence of a solvent.

MODES FOR CARRYING OUT THE INVENTION

Figure 1:
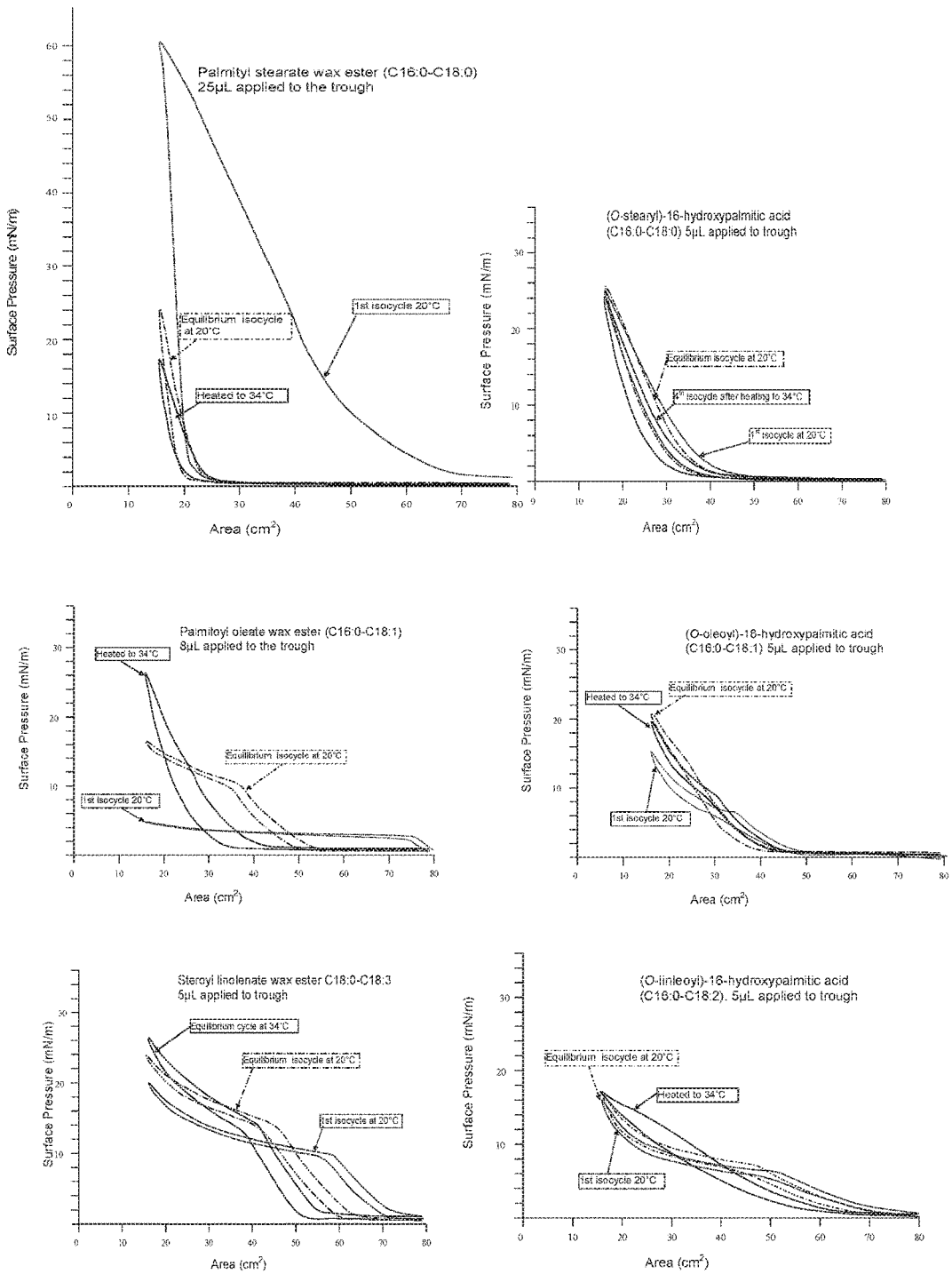
FIG. 1 shows pressure/area curves for films of three wax esters (left column of FIG. 1) and three compounds of formula (I) (right column of FIG. 1) at 20° C. and 34° C.

The present invention provides an ophthalmic formulation comprising a compound of formula (I):

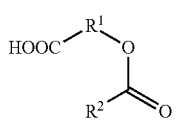

(I)

wherein
$R^1$ is a linear or branched $C_9$-$C_{33}$ alkyl or a linear or branched $C_9$-$C_{33}$ alkenyl with 1 to 4 double bonds;
$R^2$ is a linear or branched $C_9$-$C_{19}$ alkyl or a linear or branched $C_9$-$C_{19}$ alkenyl with 1 to 4 double bonds;
and an ophthalmologically acceptable carrier.

The inventors have surprisingly found that compounds of formula (I) can be used to prepare ophthalmic formulations that mimic the physico-chemical properties of tear lipids.

The tear film keeps the surface of the eye moist, lubricated and free of foreign material during blinking, protects against pathogens while also providing an optimal visually transparent medium. The most superficial layer of the tear film, the tear film lipid layer (TFLL), is 15 nm-160 nm thick. Meibomian glands in the upper and lower lids secrete tear lipids that self-assemble to form the TFLL. This layer is an essential component of the tear film and believed to enhance the spread of tears across the ocular surface, retard evaporation, and stabilise the tear film by lowering surface tension and increasing tear film break-up time. Lipid layers that are too thin or too thick can lead to inadequate spreading of the tear film or lead to decreased tear film break-up time. Currently, there is no specific component of meibomian lipids that has been correlated with poor structure or performance of the TFLL. Moreover, the actual structure of the normal TFLL is unknown.

Lipids derived from meibum are believed to form the outermost layer of tear film, which retards evaporation of water from the bulk of the tear film and from the ocular surface beneath it. Yet another function of meibum is to form a hydrophobic barrier along the margins of the eyelids to contain tear film at, and prevent it from leaking out of, the ocular surface area defined by the margins of the eyelids. These protective functions imply a very hydrophobic nature of meibum. Indeed, the major meibum components have been identified as various wax esters (WEs) and cholesteryl esters (CEs) with long-chain and very long-chain fatty acids. Triglycerides also form a significant class of compounds found in meibum, and there may be other acylglycerols present in minute amounts.

The physical properties of the compounds of formula (I) resemble the physical properties of total meibomian lipids. Surprisingly and unexpectedly, this is in stark contrast to other lipids or lipid classes found in meibomian secretions. Thus, the compounds of formula (I) can be used to prepare ophthalmic formulations that mimic the physical properties of tear lipids.

Advantageously, the films formed by compounds of formula (I), similar to meibomian lipid films, do not collapse under high pressure, and they unexpectedly increase their surface activity after cooling to 20° C. from 34° C. Further, similar to meibomian lipids but unlike wax esters, the compounds of formula (I) do not go off the aqueous surface, even under high pressures. Further, the compounds of formula (I) mix with lipids that are naturally found in tear lipids. The compounds of formula (I) also act to stabilise, and facilitate the spreading of, the tear film. The compounds of formula (I) are very surface active and, consequently, only small amounts are needed in the ophthalmic formulation of the present invention.

The present invention also provides a method for the treatment of dry eye comprising administering to a patient in need thereof a therapeutically effective amount of an ophthalmic formulation of the present invention. The present invention also provides use of a compound of formula (I) in the manufacture of an ophthalmic formulation for the treatment of dry eye.

The ophthalmic formulation of the present invention comprises a compound of formula (I):

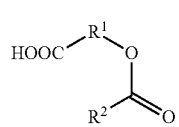

(I)

wherein
$R^1$ is a linear or branched $C_9$-$C_{33}$ alkyl or a linear or branched $C_9$-$C_{33}$ alkenyl with 1 to 4 double bonds;
$R^2$ is a linear or branched $C_9$-$C_{19}$ alkyl or a linear or branched $C_9$-$C_{19}$ alkenyl with 1 to 4 double bonds;
and an ophthalmologically acceptable carrier.

As will be apparent to a person skilled in the art, the terms "alkyl" and "alkenyl" are sometimes used herein (in relation to $R^2$ in formula (I), $R^b$, $R_1$ in Scheme 1 and $R_2$ in Scheme 1) to refer to a monovalent radical, and are sometimes used herein (in relation to $R^1$ in formula (I), and $R^a$) to refer to a divalent radical. A divalent alkyl is sometimes referred to as a "alkanediyl", and a divalent alkenyl is sometimes referred to as a "alkenediyl".

In some embodiments, $R^1$ is a linear or branched $C_9$-$C_{33}$ alkanediyl, that is, a linear or branched saturated hydrocarbon radical comprising 9 to 33 carbons. In some embodiments, $R^1$ is a linear $C_9$-$C_{33}$ alkanediyl. In some embodiments, $R^1$ is a linear or branched $C_9$-$C_{33}$ alkenediyl with 1 to 4 double bonds, that is, a linear or branched hydrocarbon radical comprising 9 to 33 carbons, and having 1, 2, 3 or 4 double bonds and no triple bonds. In some embodiments, $R^1$ is a linear $C_9$-$C_{33}$ alkenediyl with 1 to 4 double bonds.

In some embodiments, $R^1$ is a linear or branched $C_9$-$C_{17}$ alkyl or a linear or branched $C_9$-$C_{17}$ alkenyl with 1, 2 or 3 double bonds. For example, in some embodiments, $R^1$ is a linear or branched $C_9$, $C_{10}$, $C_{11}$, $C_{12}$, $C_{13}$, $C_{14}$, $C_{15}$, $C_{16}$, or $C_{17}$ alkyl, or a linear or branched $C_9$, $C_{10}$, $C_{11}$, $C_{12}$, $C_{13}$, $C_{14}$, $C_{15}$, $C_{16}$, or $C_{17}$ alkenyl with 1, 2 or 3 double bonds.

In one embodiment of the invention, HOOC—$R^1$— is selected from the group consisting of: capryl (C10:0), lauryl (C12:0), myristyl (C14:0), palmityl (C16:0), stearyl (C18:0), oleoyl (C18:1), linoleoyl (ω6) (C18:2), and linolenoyl (ω3) (C18:3).

In one embodiment of the invention, $R^2$ is a linear or branched $C_{16}$-$C_{19}$ alkyl or a linear or branched $C_{16}$-$C_{19}$ alkenyl with 1, 2, 3 or 4 double bonds. For example, in some embodiments, $R^2$ is a linear or branched $C_{16}$, $C_{17}$, $C_{18}$ or $C_{19}$ alkyl, or a linear or branched $C_{16}$, $C_{17}$, $C_{18}$ or $C_{19}$ alkenyl with 1, 2 or 3 double bonds.

In one embodiment of the invention, $R^2$ is linear or branched $C_{17}$ alkyl or a linear or branched $C_{17}$ alkenyl with 1 or 2 double bonds.

In one embodiment of the invention, $R^2$ is linear or branched $C_{19}$ alkenyl with 4 double bonds.

Examples of compounds of formula (I) include:

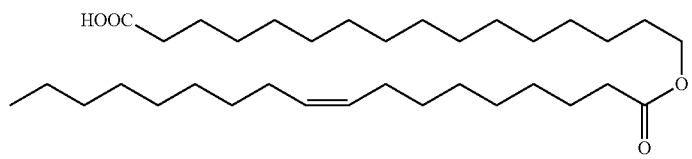

(O-oleoyl)-16-hydroxypalmitic acid (C16:0-C18:1)

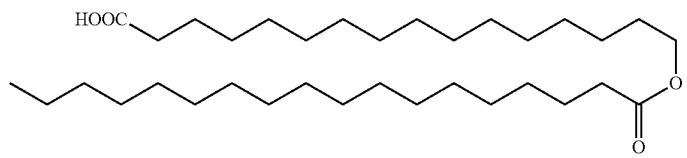

(O-stearyl)-16-hydroxypalmitic acid (C16:0-C18:0)

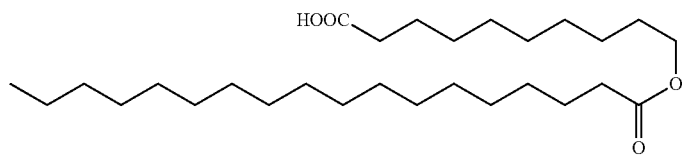

(O-stearyl)-10-hydroxycaprinic acid (C10:0-C18:0)

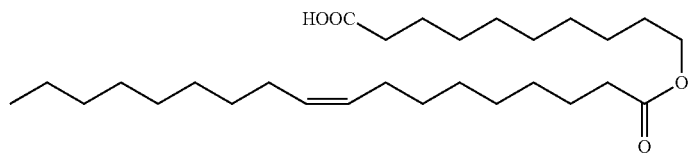

(O-oleoyl)-10-hydroxycaprinic acid (C10:0-C18:1)

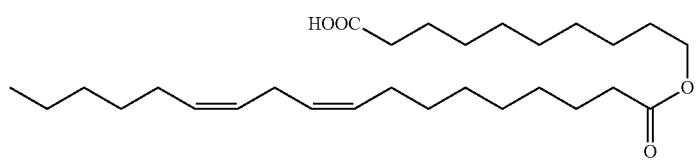

(O-linoleoyl)-10-hydroxycaprinic acid (C10:0-C18:2)

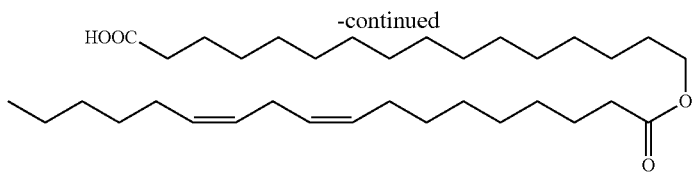

(O-linoleoyl)-16-hydroxypalmitic acid (C16:0-C18:2)

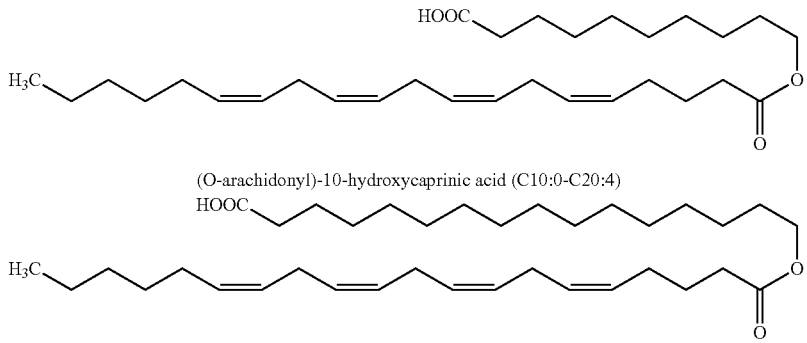

(O-arachidonyl)-10-hydroxycaprinic acid (C10:0-C20:4)

(O-arachidonyl)-16-hydroxypalmitic acid (C16:0-C20:4)

A preferred compound of formula (I) is (O-oleoyl)-16-hydroxypalmitic acid. This compound is sometimes referred to as (O-oleoyl)-ω-hydroxypalmitic acid.

The compounds of formula (I) may be present in the ophthalmic formulation of the present invention in amounts ranging from about 0.001 wt % to about 20 wt %, e.g. about 0.01 wt % to about 1 wt %, about 0.1 wt % to about 10 wt %, about 0.1 wt % to about 5 wt %, about 1 wt % to about 5 wt %, or about 2 wt % to about 4 wt %. For example, the compounds of formula (I) may be present in the ophthalmic formulation in an amount of 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.02 wt %, 0.03 wt %, 0.04 wt %, 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, or 20 wt %.

Typically, the ophthalmic formulation is a sterile formulation.

Carrier

The ophthalmic formulation of the present invention comprises an ophthalmologically acceptable carrier.

As used herein, an "ophthalmologically acceptable carrier" is an ophthalmologically acceptable solvent, suspending agent or vehicle for delivering compounds of formula (I) to the eye of a subject. The carrier may be solid or liquid. The carrier is "ophthalmologically acceptable" in the sense that the carrier is suitable for administering to the eye without causing any or a substantial adverse reaction.

Typically, the ophthalmologically acceptable carrier is, or comprises, water. Typically, the ophthalmic formulation is in the form of an eye drop or gel for application to the eye. Typically, the majority of the formulation is water. Typically, the formulation comprises greater than 50 wt % (e.g. greater than 60 wt %, 65 wt %, 70 wt %, 75 wt %, 80 wt %, 85 wt %, or 90 wt %), more typically greater than 95 wt %, water (e.g. 96 wt %, 97 wt %, 98 wt %, or 99 wt %).

In some embodiments, the ophthalmologically acceptable carrier is an oil-in-water emulsion, or an oil. In such embodiments, the ophthalmic formulation may be in the form of a cream for application to the eye. In such embodiments, the formulation may comprise greater than 10 wt %, more typically greater than 20 wt %, of an oleaginous ingredient.

In other embodiments, the carrier may be a biodegradable polymer, for example, for a biodegradable polymer ocular insert for extended release of the compound of formula (I) and optionally other compounds.

Excipients

The ophthalmic formulation typically further comprises one or more other ophthalmologically acceptable excipients.

Excipients suitable for use in the ophthalmic formulation of the present invention include, for example, demulcents, emollients, hypertonicity agents, preservatives, buffers or pH adjusting agents. Examples of suitable excipients include:

Demulcents:
  synthetic high molecular weight crosslinked polymers of acrylic acid (e.g. Carbomer 974 and Carbomer 980);
  cellulose derivatives (e.g. hydroxypropyl methylcellulose ("HPMC" or "hypromellose"), hydroxyethylcellulose, methylcellulose, carboxymethylcellulose (carmellose) or sodium carboxymethylcellulose (sodium carmellose));
  dextran (e.g. Dextran 70);
  gelatin;
  polyols (e.g. as glycerin, polyethylene glycol 300, polyethylene glycol 400, polysorbate 80, and propylene glycol);
  polyvinyl alcohol;
  povidone (polyvinylpyrrolidone);
  poloxamer; and
  hyaluronic acid (a polymer of disaccharides), or its sodium or potassium salt.

Emollients:
  lanolins (e.g. anhydrous lanolin);
  oleaginous ingredients (e.g. light mineral oil, mineral oil, paraffin, petrolatum, white ointment, white petrolatum, white wax and yellow wax); and
  castor oil.

Preservatives:
  benzalkonium chloride;
  sodium perborate;
  Oxyd (sodium chlorite 0.05%, hydrogen peroxide 0.01%);
  polyquarternium-1 (ethanol, 2,2',2"-nitrilotris-, polymer with 1,4-dichloro-2-butene and N,N,N',N'-tetramethyl-2-butene-1,4-diamine);
  sodium silver chloride;
  hexamethylene biguanide;
  oxyborate; and
  Purite® (sodium chlorite 0.005% m/v).
Ophthalmic Hypertonicity Agents:
  sodium chloride.

Preservatives

The ophthalmic formulation of the present invention may contain a preservative to inhibit microbial growth and extend the shelf-life of the formulation.

Preservatives which may be used in the ophthalmic formulation of the present invention include, for example, benzalkonium chloride, sodium perborate, Oxyd (sodium chlorite 0.05%, hydrogen peroxide 0.01%), polyquarternium-1 (ethanol, 2,2',2"-nitrilotris-, polymer with 1,4-dichloro-2-butene and N,N,N',N'-tetramethyl-2-butene-1,4-diamine), sodium silver chloride, hexamethylene biguanide, oxyborate, and Purite®. Purite® (sodium chlorite 0.005% m/v) is a microbicide with a broad spectrum of antimicrobial activity and very low toxicity to mammalian cells. Purite® preserves a formulation during storage but ultimately, following exposure to light, dissociates into water, sodium ions, chloride ions, and oxygen. Because these substances are also found in natural tears, the risk of preservative-induced ocular irritation and corneal damage is minimized. Purite® has a long history of safe and effective use. This preservative has no adverse effect on epithelial cells in vitro or in vivo, and is less disruptive to cellular integrity than many other preservatives currently used.

The ophthalmic formulation of the present invention may be prepared by any suitable means for preparing an ophthalmic formulation. Ophthalmic formulations are typically sterile and, therefore, the method may comprise a step of sterilising the ophthalmic formulation. Preferably, the ophthalmic formulation is clear and has a refractive index similar to tears, a suitable pH (usually buffered around pH 7.5) to avoid severe corneal irritation, and free of microbes. Ophthalmic formulations typically have an osmolarity value close to 300 mosmol/L. Surface tension values close to or lower than the ones observed for the tear film are generally preferred.

Oil-in-Water Emulsions

Formulations in the form of oil-in-water emulsions are effective in reducing tear evaporation, and thus useful in the management of evaporative dry eye.

In one embodiment of the invention, the ophthalmic formulation is an oil-in-water emulsion comprising a compound of formula (I), water, and optionally one or more emulsifying agents. The emulsifying agent is optional as the compounds of formula (I) can form emulsions in water without the use of an emulsifying agent. The ophthalmic formulation may also comprise one or more demulcents, emollients, hypertonicity agents, preservatives, buffers or pH adjusting agents as described above. Preferably, the ophthalmic formulation comprises one or more demulcents. The oil-in-water emulsion may be a microemulsion, where the size of an inner phase is less than a micron.

Emulsifying agents include, for example, lanolins, light mineral oil, mineral oil, paraffin, petrolatum, castor oil, as well as non-surfactant emulsifiers based on hydroxypropyl methyl cellulose, and crosslinked polymers of acrylic acid such as Pemulen™ (carbomer 1342).

Pemulen™ polymeric emulsifiers are predominantly high molecular weight polyacrylic acid polymers which have a small lipophilic (oil-loving) portion in addition to a large, hydrophilic (water-loving) portion. This chemical structure allows these copolymers to function as primary emulsifiers which actually form oil-in-water emulsions, rather than as a secondary oil-in-water emulsion stabiliser. The lipophilic portion adsorbs at the oil-water interface, and the hydrophilic portion swells in the water forming a gel network around oil droplets to provide exceptional emulsion stability to a broad range of oils.

An ophthalmic formulation of the present invention may, for example, be an oil-in-water emulsion comprising a compound of formula (I), purified water, castor oil, glycerin, polysorbate 80, carbomer 1342, and sodium hydroxide (to adjust the pH of the formulation to 7.4). The oil-in-water emulsion may be packaged in a single dose vial containing 0.4 mL.

An exemplary ophthalmic formulation of the present invention is a formulation in the form of an oil-in-water emulsion comprising the following:

| | |
|---|---|
| Compound of formula (I) | 0.1 wt % to 5 wt % |
| Purified water | >80 wt % |
| castor oil | 1 wt % to 10 wt % |
| glycerin | 0.2 wt % to 1 wt % |
| polysorbate 80 | 0.2 wt % to 1 wt % |
| carbomer 1342 | 0.1 wt % to 4 wt % |
| sodium hydroxide | <0.1 wt % |
| sodium chloride | 0.1 wt % to 2 wt % |
| TOTAL: | 100 wt % |

In another embodiment of the invention, the ophthalmic formulation is an oil-in-water emulsion comprising a compound of formula (I), water, and one or more ophthalmologically acceptable excipients selected from the group consisting of polyethylene glycol, propylene glycol, glycerin, polyvinyl alcohol, povidone, polysorbate 80, hydroxypropyl methylcellulose, carmellose, carbomer 980, sodium hyaluronate, dextran, and the like.

An ophthalmic formulation of the present invention may, for example, comprise a compound of formula (I), water, hydroxypropyl methylcellulose, polysorbate 80, disodium phosphate and sodium chloride. The ophthalmic formulation may be packaged in a single dose vial containing 0.5 mL.

Another exemplary ophthalmic formulation of the present invention is a formulation in the form of an oil-in-water emulsion comprising the following:

| | |
|---|---|
| Compound of formula (I) | 0.1 wt % to 5 wt % |
| Purified water | >85 wt % |
| hydroxypropyl methylcellulose | 0.1 wt % to 4 wt % |
| polysorbate 80 | 0.2 wt % to 1 wt % |
| disodium phosphate | 0.1 wt % |
| sodium hydroxide | <0.1 wt % |
| sodium chloride | 0.1 wt % to 2 wt % |
| TOTAL: | 100 wt % |

Ophthalmic Formulations Containing Active Pharmaceutical Ingredients

Ophthalmic formulations of the present invention comprising an aqueous carrier may be used as an artificial tear and may be used to treat dry eye. Thus, in some embodiments, the ophthalmic formulation is an artificial tear formulation. The ophthalmic formulation may also be used as a vehicle for delivering an active pharmaceutical ingredient to the eye of a patient.

Thus, the ophthalmic formulation of the present invention may comprise an active pharmaceutical ingredient for treating, for example, a condition or disease of the eye. The active pharmaceutical ingredient may, for example, be an anti-inflammatory agent (e.g. a corticosteroid such as loteprednol etabonate, fluorometholone or dexamethasone phosphate), an anti-immune response agent (e.g. cyclosporine A, pimecrolimus and voclosporin), or an antibiotic (e.g. doxycycline).

In one embodiment of the invention, the ophthalmic formulation contains liposomes incorporating the active pharmaceutical ingredient.

Liposomes can be employed to incorporate active pharmaceutical ingredients in the oily or in the hydrophilic phase of a formulation. The bioavailability of a drug administered by eye drops can be enhanced through the use of liposomes. Liposomes are artificially prepared vesicles composed mainly of phospholipids. A lipophilic drug will bind within the vesicle membranes, while a hydrophilic drug will become encapsulated within the aqueous phase in the interior of the liposome.

Depending on the charge of the phospholipids, liposomes can be positive, negative or neutral. Liposomes may be prepared from positive charged phospholipids. The vesicles are suspended in aqueous solutions with high viscosity polymers (e.g. hydroxyethylcellulose, methylcellulose, hydroxypropylmethylcellulose) and vinylic derivatives (e.g. polyvinylpirrolidone, polyvinyl alcohol) and their mixtures. Neutral liposomes may be prepared from phosphatidylcholine associated with mucoadhesive polymers.

Delivery of the Ophthalmic Formulation

The ophthalmic formulation of the present invention may be delivered to the patient in the form of an eye drop (in a single-dose or multi-dose dropper), ointment, gel, cream or biodegradable polymer ocular insert (designed for extended-release), or by ocular humidification (e.g. a multi-dose spray).

To treat dry eye, the ophthalmic formulation of the present invention is typically administered to the eye in an amount to provide 5 to 10 microgram of the compound of formula (I) to the eye.

The packaging of the ophthalmic formulation should correlate to the preserved or non-preserved nature of the solution. Packaging approaches such as form-fill-seal technology, which merges blow molding, sterile filling, and hermetic sealing into a single process, can be especially useful for packaging preservative-free formulations in unit dose containers. Typically, these single-dose containers are made of low-density polyethylene or polypropylene and incorporate a twist-off closure.

Preparation of the Compounds of Formula (I)

The compounds of formula (I) may be prepared by methods known in the art for the synthesis of organic compounds.

For example, the following general method may be used to prepare compounds of formula (I):

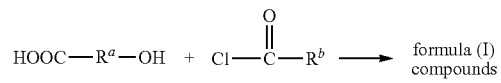

In the above formulae for the starting materials, $R^a$ can be a linear or branched $C_9$-$C_{33}$ alkyl or a linear or branched $C_9$-$C_{33}$ alkenyl with 1 to 4 double bonds, and $R^b$ can be a linear or branched $C_9$-$C_{19}$ alkyl or a linear or branched $C_9$-$C_{19}$ alkenyl with 1 to 4 double bonds. The starting material compounds are mixed in a molar ratio of about 1:1 in a suitable organic solvent (e.g. chloroform, tetrahydrofuran or dichloromethane) at room temperature overnight (about 12 hours).

In the above method, no solvent is required if one of the starting materials is a liquid at the reaction conditions applied. Most acid chlorides are liquid at room temperature; accordingly, the use of a solvent can be omitted from the above method. Thus, the present invention also provides a method for the preparation of the compounds of formula (I) comprising mixing the starting material compounds in a molar ratio of, for example, about 1:1 at a temperature of from about room temperature to about 60° C. overnight (e.g. about 12 hours). Advantageously, circumventing the use of solvents avoids the use of quantitative amounts of base (HCl is released as a gas) and minimises water contamination; water can interfere with the reaction by destroying the acid chloride starting compound.

Typically, acid chlorides are used in the reaction to prepare the compounds of formula (I). However, acid bromides may also be used.

The above method can, for example, be used to prepare the following compounds:

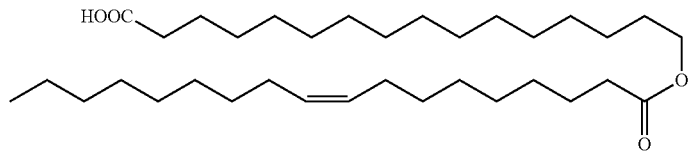

(O-oleoyl)-16-hydroxypalmitic acid (C16:0-C18:1)
prepared from ω-hydroxypalmitic acid with oleic acid

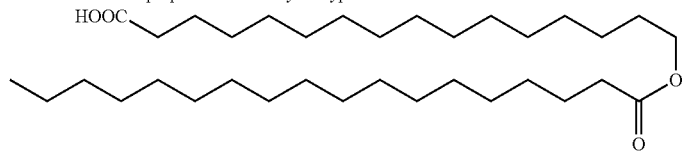

(O-stearyl)-16-hydroxypalmitic acid (C16:0-C18:0)
prepared from ω-hydroxypalmitic acid with stearic acid

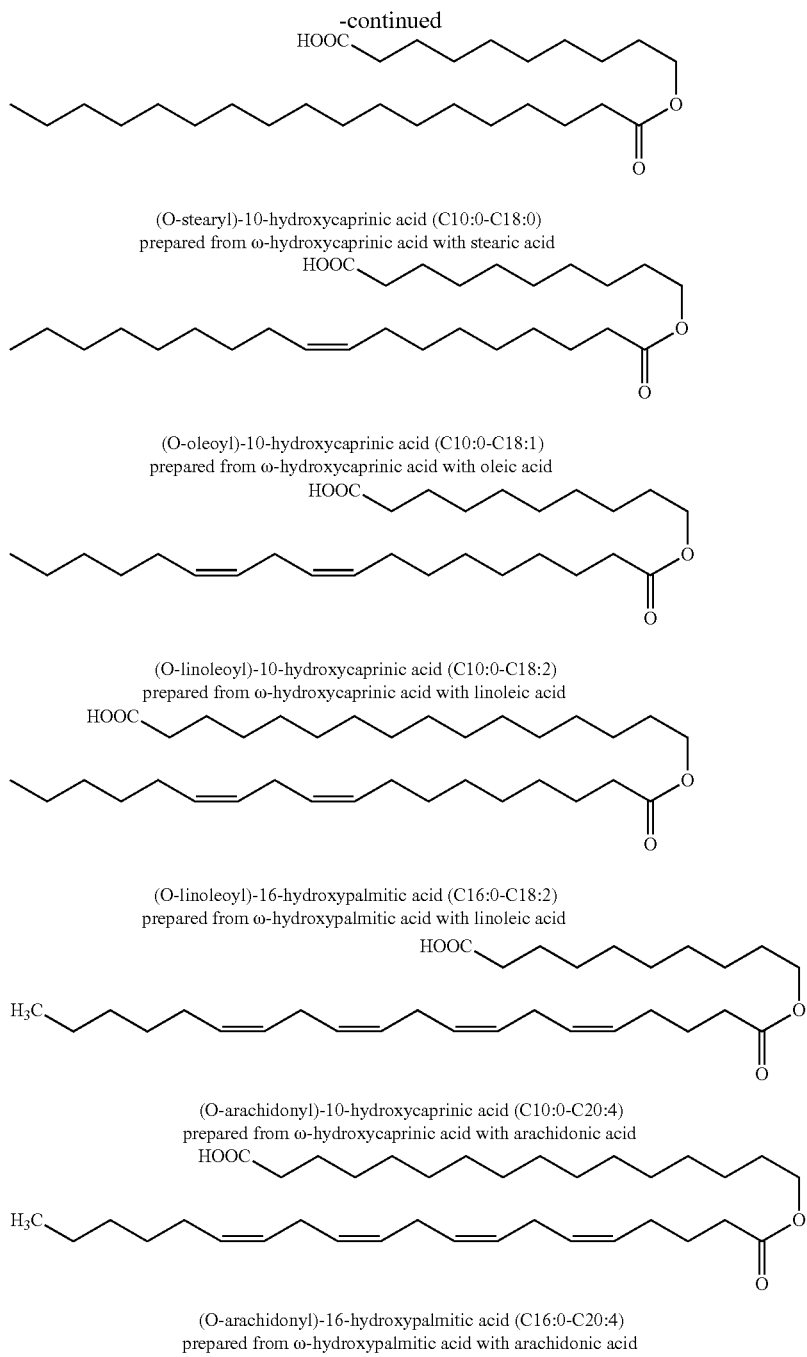

Long chain mono-unsaturated ω-hydroxy fatty acids or their relevant esters for use as starting materials for the above method can, for example, be prepared via cross-metathesis reactions as shown in Scheme 1 below. In Scheme 1 below, $R_1$ and $R_2$ are alkyl groups. Depending on the number of a and b, different chain lengths and positions of the double bonds can be achieved. Omega vinyl functionalised educts as outlined are preferable for this kind of synthesis to minimise undesired mixed cross-metathesis reactions. By using commercially available educts with double bonds at positions varying from Δ3 to Δ14, chain lengths up to $C_{30}$ are realisable with double bonds between Δ3 to Δ14.

Scheme 1

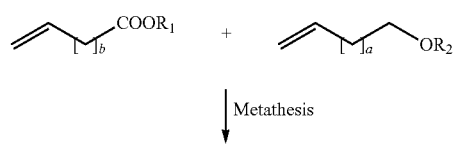

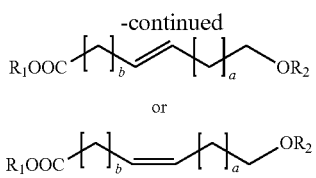

The saturated forms of the products in the above scheme can be produced by hydration.

The free ω-hydroxy fatty acids can be released by hydrolysis for use in the esterification reaction to form the compounds of formula (I).

16-Hydroxypalmitoleic acid (16-hydroxyhexadecenoic acid) can be synthesised from aleuritic acid via the available vicinal diol through a stereoselective elimination of its threo or erthyro form to the desired product in cis- or trans-form, as shown Scheme 2 below.

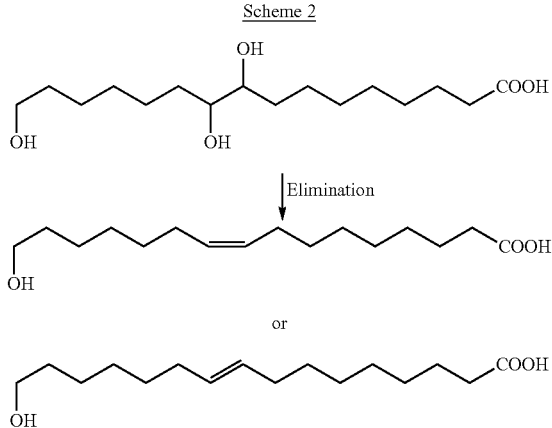

In the specification and the appended claims, singular forms, including the singular forms "a," "an" and "the", specifically also encompass the plural referents of the terms to which they refer unless the context clearly dictates otherwise. In addition, as used herein, unless specifically indicated otherwise, the word "or" is used in the "inclusive" sense of "and/or" and not the "exclusive" sense of "either/or".

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable, which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value, for variables which are inherently continuous.

The formulations and methods of the present invention are intended for use with any subject that may experience the benefits of the formulations and methods of the invention. The subject is typically a mammal, more typically a human. However, the invention is not limited to the treatment of humans and is applicable to veterinary uses. Thus, in accordance with the invention, the term "subject" or "subject in need thereof" includes humans as well as non-human animals, such as domesticated mammals including, without limitation, cats, dogs, and horses.

The term "therapeutically effective amount" is used to denote treatments at dosages effective to achieve the therapeutic result sought.

Reference is made hereinafter in detail to specific embodiments of the invention. While the invention is described in conjunction with these specific embodiments, it will be understood that it is not intended to limit the invention to such specific embodiments. On the contrary, it is intended to cover alternatives, modifications, substitutions, variations and equivalents as may be included within the spirit and scope of the invention as defined by the appended claims.

EXAMPLES

Materials Used and General Methods

Oleoyl chloride (Sigma Aldrich product no. 367850); 16-hydroxyhexadecanoic acid (Sigma Aldrich product no. 177490); stearoyl chloride (Sigma product no. 171158); linoleoyl chloride (Sigma Aldrich product no. L-5753); 10-hydroxydeconoic acid (Sigma Aldrich product no. 379700); Silica gel 70-230 mesh 60 Å (Sigma Aldrich product no. 112926-00-8); Silica gel (Sigma Aldrich product no. 28862); Sephadex LH-20 (Sigma Aldrich product no. 17-0090-01), GE Healthcare 17-0090-10. Chloroform, ethanol-free chloroform (Sigma Aldrich product no. 372978), methanol, n-hexane, diethylether (water-free), tetrahydrofuran (water-free), and acetic acid were all of analytic grade and purchased from Sigma Aldrich (Castle Hill, Australia). The chloroform used in the examples was either purchased in alcohol-free form (Sigma Aldrich product no. 372978), or was further purified prior to use by distillation to remove the stabiliser ethanol. Palmityl oleate and oleic acid were purchased from NuCheck (Elysian Minn., USA).

TLC analysis: mobile phase n-hexane:diethylether:acetic acid (80:20:1), detection by iodine fume or charcoal stain using 5% vol/vol concentrated sulfuric acid in ethanol followed by heating the TLC plates to 150° C. TLC plates: Silicagel 60 Å F254, 0.2 mm on aluminum support (Sigma Z191293 or Riedel-deHaen 37360).

The physico-chemical properties of certain wax esters, meibomian lipids, and compounds of formula (I) alone or mixed with human meibum were characterized on a Langmuir-Blodgett minitrough by means of surface pressure-area (Π-A) measurements.

Example 1: Synthesis and purification of (O)-oleoyl-ω-hydroxypalmitic acid (C16:0-C18:1)

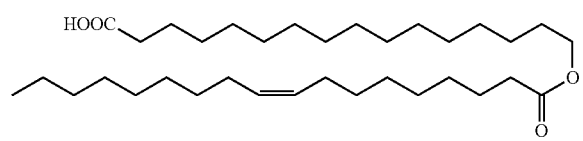 [SMILES: CCCCCCCC/C=C\CCCCCCCC(=O)OCCCCCCCCCCCCCCCC(=O)O]

16-Hydroxyhexadecanoic (6.5 mg, $2.3 \times 10^{-5}$ mol) was dissolved in 500 μL CHCl$_3$ in a glass vial and oleoylchloride (18 μL, $5.6 \times 10^{-5}$ mol) was added. The reaction mixture was stirred at room temperature for 24 hours and then loaded onto a 25×1 cm silica gel column equilibrated with CHCl$_3$ as the mobile phase. 1.5 mL fractions were collected and analysed by UV/VIS absorption (200-300 nm). Positive fractions were then further analysed by TLC and FT-IR. Fractions containing the resultant compound of formula (I)

(as evident by a band in TLC which represents a compound with two —C═O functions visible at around 1700 cm$^{-1}$ in the FT-IR) were pooled and chloroform removed under a dry nitrogen stream. The residue was resuspended in about 1 mL of methanol and 250 μL was loaded onto a 25×1 cm Sephadex LH-20 column at a flow rate of 0.5 mL/min with methanol as the mobile phase. Fractions of 1.5 mL size were analyzed as described before and pure product was found in the first two UV/VIS positive fractions. Finally the methanol was removed under a nitrogen stream and the product stored at −20° C. under nitrogen. In order to characterize its physico-chemical properties the product was resuspended in chloroform.

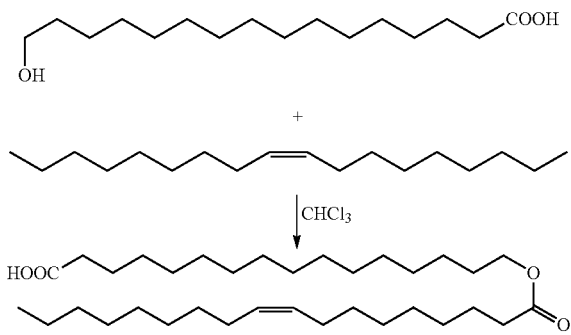

Example 2: Synthesis and purification of (O)-stearyl-16-hydroxypalmitic acid (C16:0-C18:0) and (O)-stearyl-10-hydroxydecanoic acid (C10:0-C18:0)

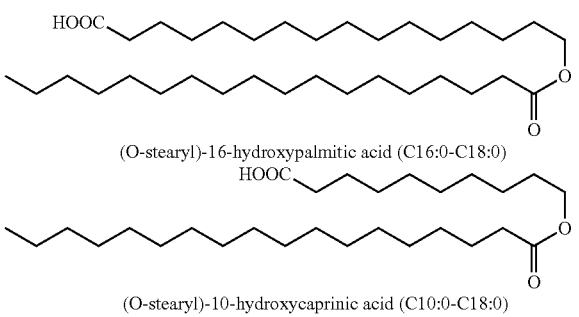

(O-stearyl)-16-hydroxypalmitic acid (C16:0-C18:0)

(O-stearyl)-10-hydroxycaprinic acid (C10:0-C18:0)

Stearoyl chloride (30 μmol, 9.1 mg) and either 16-hydroxyhexadecanoic acid (8.4 mg) or 10-hydroxydecanoic acid (5.6 mg) were dissolved in water-free tetrahydrofuran (THF) (400 μL) in a closed 3 mL glass vial and the reaction mixture was stirred at room temperature for 24 hours. The crude product was crystallised by cooling the reaction mixture to −80° C., the supernatant was removed and the product washed with −80° C. pre-cooled THF (1 mL). Recrystallization in THF (400 μL) and washing with THF (1 mL) at −80° C. was repeated once. The resulting crude product was dissolved in as little methanol as possible (around 1.5 mL) and 500 μL was loaded onto a 25×1 cm Sephadex LH-20 column at a flow rate of 0.5 mL/min with methanol as the mobile phase. Fractions of 1.5 mL size were analyzed by UV-VIS spectroscopy, TLC, FT-IR and electrospray mass spectrometry. The pure product of either (O)-stearyl-16-hydroxypalmitic acid (C16:0-C18:0) or (O)-stearyl-10-hydroxydecanoic acid (C10:0-C18:0) was found in the first UV/VIS positive fractions. Finally the methanol was removed under a nitrogen stream and the product stored at −20° C. under nitrogen.

Example 3: Synthesis and purification of (O)-oleoyl-10-hydroxydecanoic acid (C10:0-C18:1)

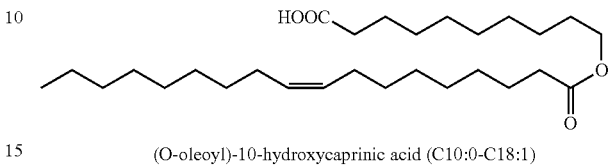

(O-oleoyl)-10-hydroxycaprinic acid (C10:0-C18:1)

10-Hydroxydecanoic acid (5.6 mg, 30 μmol) was dissolved in water-free THF (500 μL) and oleoyl chloride (19 μL, 60 μmol) was added. The reaction mixture was stirred over night (12 hours) in a closed 3 mL glass vial. The solvent was removed under nitrogen and 0.1 N sodium hydroxide solution (300 μL) was added and the suspension mixed for 10 minutes. Then 2 N hydrogen chloride solution (25 μL) was added and the suspension extracted twice with chloroform (500 μL). The chloroform phases were combined, dried under nitrogen and the crude product re-suspended in as little methanol as possible (around 2 mL). 500 μL was loaded onto a 25×1 cm Sephadex LH-20 column at a flow rate of 0.5 mL/min with methanol as the mobile phase. Fractions of 1.5 mL size were analyzed by UV-VIS spectroscopy, TLC and FT-IR. Fractions containing the product were pooled, dried under nitrogen and applied again to the same column. The pure product was finally identified by electrospray mass spectrometry, dried under nitrogen and stored at −20° C.

Example 4: Synthesis and purification of (O-linoleoyl)-10-hydroxycaprinic acid (C10:0-C18:2) and (O-linoleoyl)-16-hydroxypalmitic acid (C16:0-C18:2)

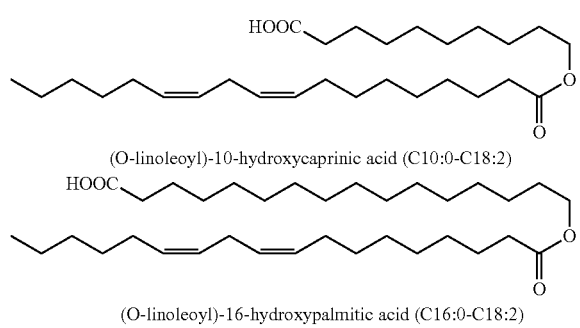

(O-linoleoyl)-10-hydroxycaprinic acid (C10:0-C18:2)

(O-linoleoyl)-16-hydroxypalmitic acid (C16:0-C18:2)

Either 10-hydroxydecanoic acid (30 μmol, 5.6 mg) or 16-hydroxypalmitic acid (30 μmol, 8.1 mg) was dissolved in water-free THF (500 μL), and linoleoyl chloride (33 μmol, 10 μL) was added. The reaction mixture was stirred overnight (12 hours) in a closed 3 mL glass vial. The solvent was removed under nitrogen and re-dissolved in chloroform (500 μL). A portion (250 μL) of each of these solutions was loaded onto a 25×1 cm Sephadex LH-20 column equilibrated with chloroform. Fractions of 1.5 mL size were collected at a flow rate of 1 mL/min and analyzed by UV-VIS spectroscopy, TLC and FT-IR. Fractions containing the product were dried under nitrogen and re-dissolved in chloroform to give a concentration of 1 mg/mL and stored at −20° C. The pure product was identified by electrospray mass spectrometry.

Other compounds of formula (I), such as (O-arachidonyl)-10-hydroxycapric acid and (O-arachidonyl)-16-hydroxypalmitic acid, can be prepared in a similar manner to that described above.

Example 5: Surface Pressure-Area (Π-A) Measurements

A buffer (NaCl: 6.63 g/L, KCl: 1.72 g/L, NaHCO$_3$: 1.38 g/L, CaCl$_2$.2H$_2$O: 0.15 g/L, NaH$_2$PO$_4$.H$_2$O: 0.10 g/L and MOPS: 4.18 g/L dissolved in MilliQ water) was added to a double barrier minitrough (Nima Technology Ltd, UK; Working surface area 15 cm$^2$–80 cm$^2$). Purified preparations of wax esters in chloroform (1 mg/mL), meibomian lipids in chloroform (1 mg/mL), and compounds of formula (I) in chloroform (ranging from 1.4 μmol to 0.1 μmol) alone or mixed with human meibum at different ratios, were spread on the surface (air-buffer interface) of the buffer subphase. Dynamic Π-A profiles of films at the air-buffer interface of the Langmuir trough were collected using software supplied by NIMA Technology. Surface pressure was monitored using a paper plate connected to a Wilhelmy balance. Compression and expansion cycles were conducted over an area (A) of 79 cm$^2$–16 cm$^2$ at a barrier rate of 15 cm$^2$/min and at a temperature of 20° C. and 34° C. The results are shown in FIGS. 1 to 3.

FIG. 1 shows pressure/area curves comparing dynamic surface pressure of films of wax esters (top to bottom: palmityl stearate wax ester (C16:0-C18:0) (25 μL applied to the trough); palmitoyl oleate wax ester (C16:0-C18:1) (8 μL applied to the trough); and steroyl linolenate wax ester (C18:0-C18:3) (5 μL applied to the trough)) (left column of FIG. 1) with their equivalent or similar compound of formula (I) (top to bottom: (O-stearyl)-16-hydroxypalmitic acid (C16:0-C18:0) (5 μL applied to the trough); (O-oleoyl)-16-hydroxypalmitic acid (C16:0-C18:1) (5 μL applied to the trough); and (O-linoleoyl)-16-hydroxypalmitic acid (C16:0-C18:2) (5 μL applied to the trough)) (right column of FIG. 1) at 20° C. and 34° C. A major difference observed is that the films comprising the compound of formula (I) do not collapse whereas the wax esters do. This is indicated by the take-off moving to the left of the x-axis (indicating collapse), whereas the take-off for the compounds of formula (I) remains constant. This data also shows that the compounds of formula (I) are very surface active, i.e. a small amount has high surface activity.

Figure 2:
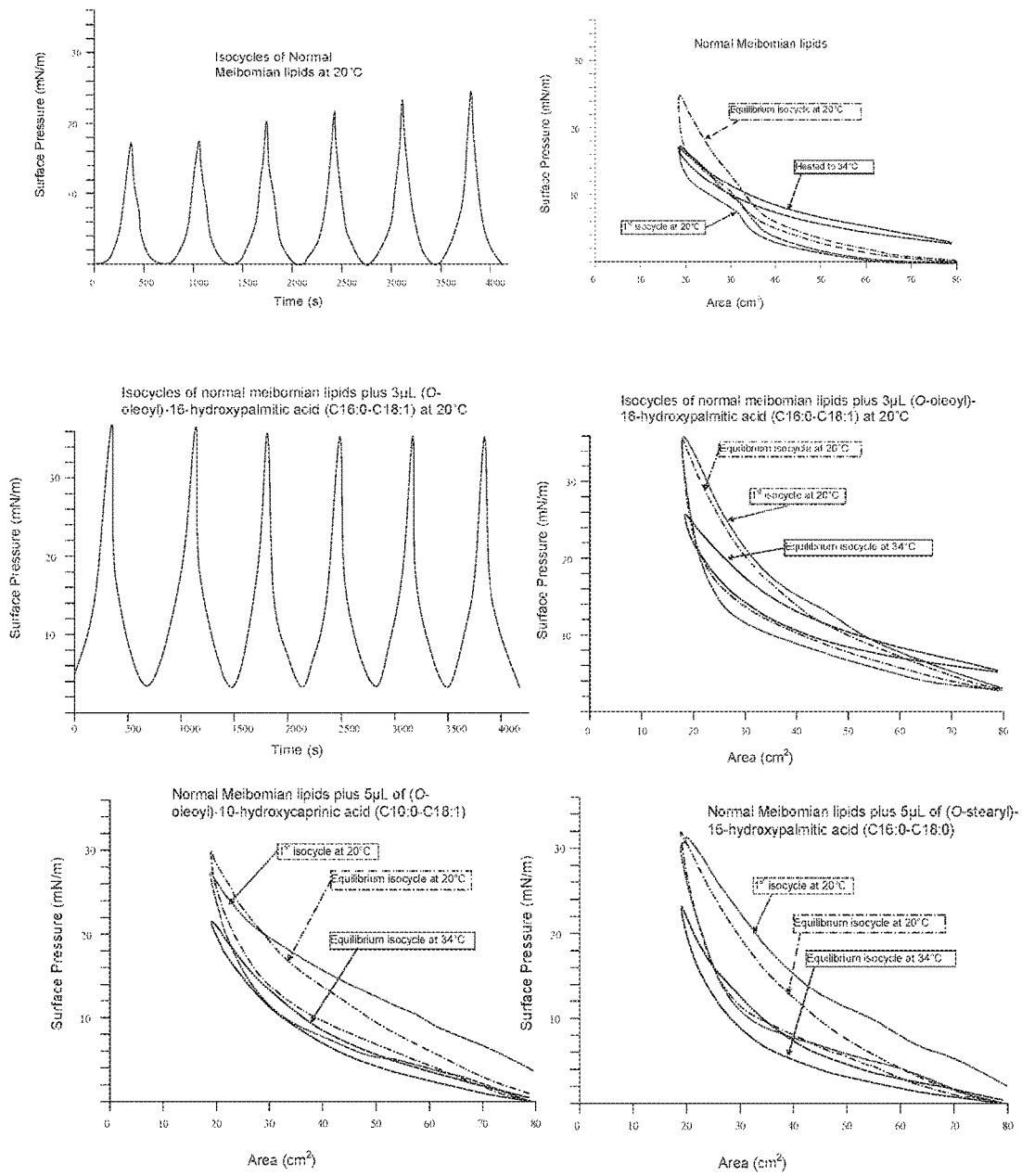
FIG. 2 shows pressure/time and pressure/area curves for meibomian lipids (25 µL) alone (top two graphs), pressure/time and pressure/area curves for a mixture of meibomian lipids with 3 µL of (O-oleoyl)-16-hydroxypalmitic acid (middle two graphs), pressure/area curves for a mixture of meibomian lipids with 5 μL of (O-oleoyl)-10-hydroxycaprinic acid (bottom left graph), and pressure/area curves for a mixture of meibomian lipids with 5 μL of (O-stearyl)-16-hydroxypalmitic acid (bottom right graph).

FIG. 2 shows pressure/time and pressure/area curves showing the dynamic surface pressure of films of meibomian lipids (25 μL) alone and mixtures of meibomian lipids (20 μL) with different compounds of formula (I) ((O-oleoyl)-16-hydroxypalmitic acid (C16:0-C18:1) (3 μL), middle row; (O-oleoyl)-10-hydroxycaprinic acid (C10:0-C18:1) (5 μL), bottom row, left; and (O-stearyl)-16-hydroxypalmitic acid (C16:0-C18:0) (5 μL), bottom row, right). The pressure/time curve for meibomian lipids alone indicates that it takes a long time for the lipids to stabilise on the surface (pressure increasing at each cycle). Adding a small amount of a compound of formula (I) causes fast stabilisation of the film (indicated on the pressure/time curve with the mixture having little change between isocycles) and the maximum surface pressures are much higher. Higher surface pressures (low surface tension) have been shown to be associated with a stable tear film. All of the different examples of the compounds of formula (I) interact readily with meibomian lipids and stabilise the films.

Figure 3:
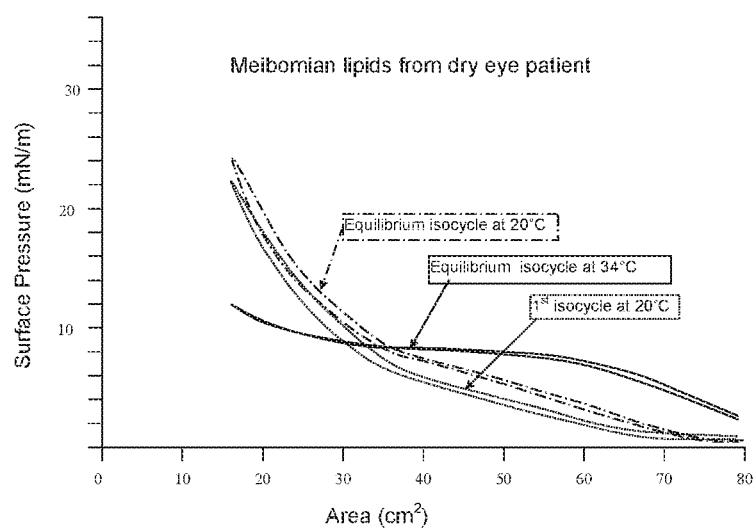
FIG. 3 shows pressure/area curves of a film of meibomian lipids alone from a patient with dry eye disease (top graph), and a film of the meibomian lipids with 3 μL of (O-oleoyl)-16-hydroxypalmitic acid (C16:0-C18:1) (bottom graph).
Figure 3:
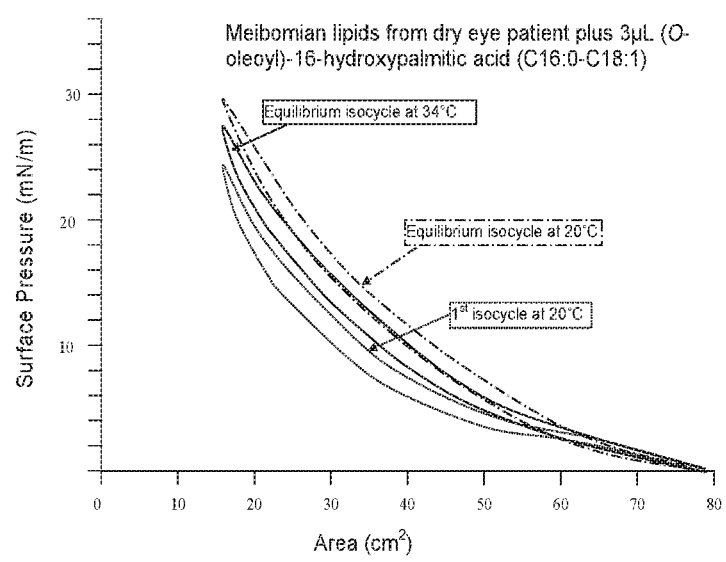

FIG. 3 shows pressure/area curves showing the dynamic surface pressure of films of meibomian lipids alone from a patient with dry eye disease and mixtures of the meibomian lipids with a compound of formula (I) ((O-oleoyl)-16-hydroxypalmitic acid (C16:0-C18:1) (3 μL)). The compound of formula (I) increases the surface pressure, which is an advantage in dry eye, and causes an increase in hysteresis which means that the lipid layer has become more viscous indicating that it spreads more evenly and is more resistant to rapid changes.

Example 6: Comparison of (O-oleyl)-ω-hydroxypalmitic acid with Other Components of the Meibum To evaluate the role of a compound of formula (I) in tear films, (O-oleoyl)-w-hydroxypalmitic acid was used as an example of a compound of formula (I) and compared with structurally-related palmityl oleate wax ester and oleic acid by employing a Langmuir trough.

Freshly synthesised (O-oleoyl)-ω-hydroxypalmitic acid (an example of a compound of formula (I)) was spread either alone or mixed with human meibum on a Langmuir trough on an artificial tear buffer. Pressure-area isocycle profiles were recorded and compared with those of palmityl oleate and oleic acid, alone or mixed with meibum. These measurements were accompanied by fluorescence microscopy of meibum mixed films during pressure-area isocycles.

As discussed below, it was found that pure films of (O-oleoyl)-w-hydroxypalmitic acid are as surface active as oleic acid films, cover a much larger surface area than either palmityl oleate or oleic acid, and show a distinct biphasic pressure-area isocycle profile. All these properties can be explained by (O-oleoyl)-ω-hydroxypalmitic acid binding weakly to the aqueous surface via an ester group and strongly via a carboxyl group. Whereas palmityl oleate films arrange as multi-layered structures and oleic acid tends to disappear into the subphase, the (O-oleoyl)-ω-hydroxypalmitic acid molecules are maintained on the aqueous surface and show only a minor re-arrangement into multi-layered structures during repetitive pressure area isocycles. When mixed with meibum, similar features as for pure films were observed. In addition, meibum films mixed with (O-oleoyl)-ω-hydroxypalmitic acid appear very homogeneous, which is a feature not seen with the mixtures with palmityl oleate and oleic acid. (O-Oleoyl)-ω-hydroxypalmitic acid was thus found to be a potent surfactant; this is property that is important in spreading and stabilising meibomian lipid films.

The data presented below supports that compounds of formula (I) are potent surfactants which can facilitate spreading and stabilising meibomian lipid films.

6.1 Synthesis and purification of (O-oleoyl)-ω-hydroxypalmitic acid

Omega-hydroxypalmitic acid (6.8 mg; 25 μmol) was mixed with oleoyl chloride (32.5 μmol) in a 1.5 mL glass vial and incubated overnight at 60° C. with continuous agitation based on the method described in Ranu et al. (Ranu B C, Dey S S, Hajra A, 2002, "Highly efficient acylation of alcohols, amines and thiols under solvent-free and catalyst-free conditions", *Green Chemistry*, 5: 44-46, incorporated herein by reference). After incubation, partial purification was carried out using a silica gel column (70-230 mesh, 60 Å at 30×1 cm) equilibrated with n-hexane: diethylether: acetic acid (4:1:0.05). The reaction mixture was suspended in 500 μL of ethanol-free chloroform and applied in two lots to the column and developed with n-hexane: diethylether: acetic acid (4:1:0.05) at a flow rate of 1 mL/min. Fractions (1 mL) were collected and analysed by FT-IR and TLC. TLC plates were treated with iodine or charred after treatment with sulfuric acid (5% in ethanol) for visualisation. Fractions containing the desired product were pooled, dried under nitrogen, resuspended in 200 μL pre-chilled chloroform:methanol:acetic acid (2:1:0.01) and further purified using a Sephadex LH-20 column (30×1 cm) equilibrated with the same solvent at a flow rate of 0.5 mL/min. Fractions of 1.5 mL were collected and analysed as described above and those containing pure product were pooled, dried and weighed. A stock solution of 1 mg/mL (1.86 mM) in chloroform was prepared and stored at −20° C.

6.2 Preparation of Human Meibomian Lipids

Collection of meibomian lipids was in accordance with the Tenets of Helsinki. Human meibomian lipids were gently squeezed out of the meibomian glands of a single 56-year old male subject's lower eyelids by applying pressure to the eyelids using sterile cotton swabs on either side of the lid. Multiple collections were carried out and pooled to provide consistency in the experiments. The subject was devoid of any external signs or symptoms of ocular pathology including dry eye disease. The expressed lipids were harvested using a sterile stainless steel spatula and dissolved in chloroform. The meibomian lipids were dried through vacuum concentration and centrifugation, and then reconstituted in chloroform spiked with 0.5% (w/w) of the fluorophore, 1-palmitoyl-2-[12-[(7-nitro-2-1,3-benzoxadiazol-4-yl) amino]dodecanoyl]-sn-glycero-3-phosphatidylcholine] (NBD-DPPC) (Avanti Polar Lipids, Auspep Pty. Ltd (Tullamarine, Australia)) and stored at −20° C. until used.

6.3 Surface Pressure-Area (Π-A) Measurements

The surface characteristics of (O-oleoyl)-ω-hydroxypalmitic acid were compared with palmityl oleate (a structurally similar wax ester) and oleic acid (which is equivalent to the fatty acid (amphiphilic) component of (O-oleoyl)-ω-hydroxypalmitic acid).

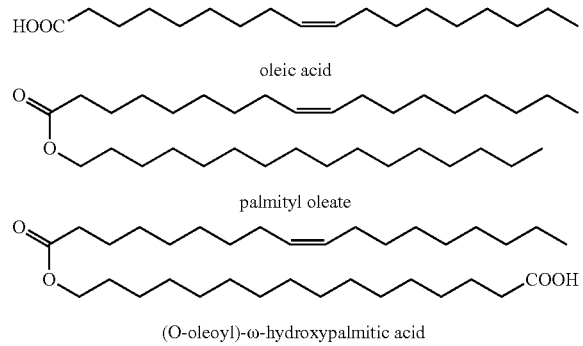

Films were formed by spreading 7.5 nmol of the lipids dissolved in chloroform onto the cleaned surface (air-buffer interface) of an artificial tear buffer (NaCl: 6.63 g/L, KCl: 1.72 g/L, NaHCO$_3$: 1.38 g/L, CaCl$_2$.2H$_2$O: 0.15 g/L, NaH$_2$PO$_4$×H$_2$O: 0.10 g/L and MOPS: 4.18 g/L dissolved in ion exchange ultrapure water) in a double barrier 80 mL temperature-controlled (35° C.) Langmuir trough (Nima Technology Ltd, UK). After 5 isocycles were obtained, the temperature was lowered to 20° C. A Whilhelmy balance (Whatman No. 1 filter paper) was used to record surface pressure during isocycles (79 cm$^2$-16 cm$^2$ at 10 cm$^2$/min).

The results were compared with mixtures with meibomian lipids. Human meibum (20 μg) was mixed with ~10 mol % (O-oleoyl)-ω-hydroxypalmitic acid (2 μg) or with palmityl oleate (1.9 μg) or oleic acid (1.1 μg). These mixtures were spread at 20° C. and 5 isocycles carried out. The film was then heated to 35° C. for another 5 isocycles. The Π-A curves were compared with those for pure meibomian lipid films. In some cases, meibomian lipids doped with 0.5% (w/w) NBD-DPPC were used in order to view the films microscopically.

6.4 Results

Pressure-Area (Π-A) Isocycles of Lipid Films

Figure 4:
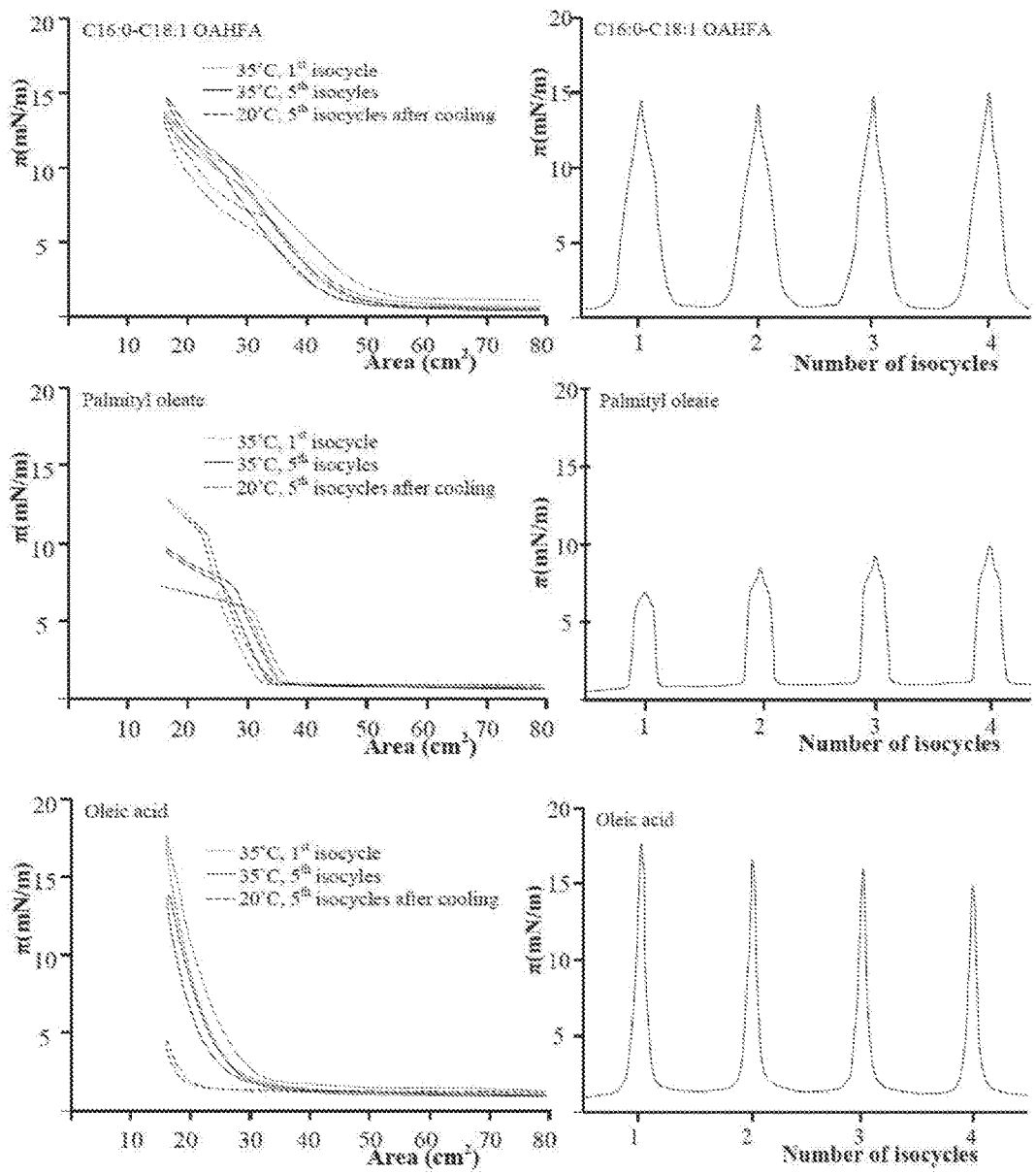
FIG. 4 shows surface pressure/area curves for a film of 7.5 nmol (corresponding to 4 μg (O-acyl)-ω-hydroxy fatty acid (OAHFA)) of (O-oleoyl)-16-hydroxypalmitic acid (top figure, left column), palmityl oleate (middle figure, left column), and oleic acid (bottom figure, left column) showing the first and fifth isocycles at 35° C. and the fifth isocycle after cooling to 20° C. The right column of FIG. 4 shows time-pressure analysis of the first four isocycles at 35° C. after spreading.

FIG. 4 shows surface pressure/area curves for equimolar amounts of pure lipid films spread at 35° C. and then recordings after the same films were cooled to 20° C.

The (O-oleoyl)-ω-hydroxypalmitic acid was very surface active as indicated by its large take-off area and there was little change in its profile through repeated isocycles. For palmityl oleate, there was a slow shift in the Π-A curve to the left and an increase in maximum surface pressure ($\Pi_{max}$) with increasing isocycles. Without wishing to be bound by theory, the inventors have interpreted this as molecules leaving the surface and moving into the outer, non-polar lipid phase. This contrasts markedly with oleic acid, which both decreases in take-off and in $\Pi_{max}$ as isocycles continue and there is no phase shift. This is indicative of molecules moving off the surface into the subphase. This could occur because either oleic acid is partly miscible in the artificial tear buffer, or micelles could form. Both are possible given that the critical micellar concentration of oleic acid is about 6 μM and energy is put into this system by compression.

Surfactant Properties of Meibomian Films Mixed with Model Lipids

Figure 5:
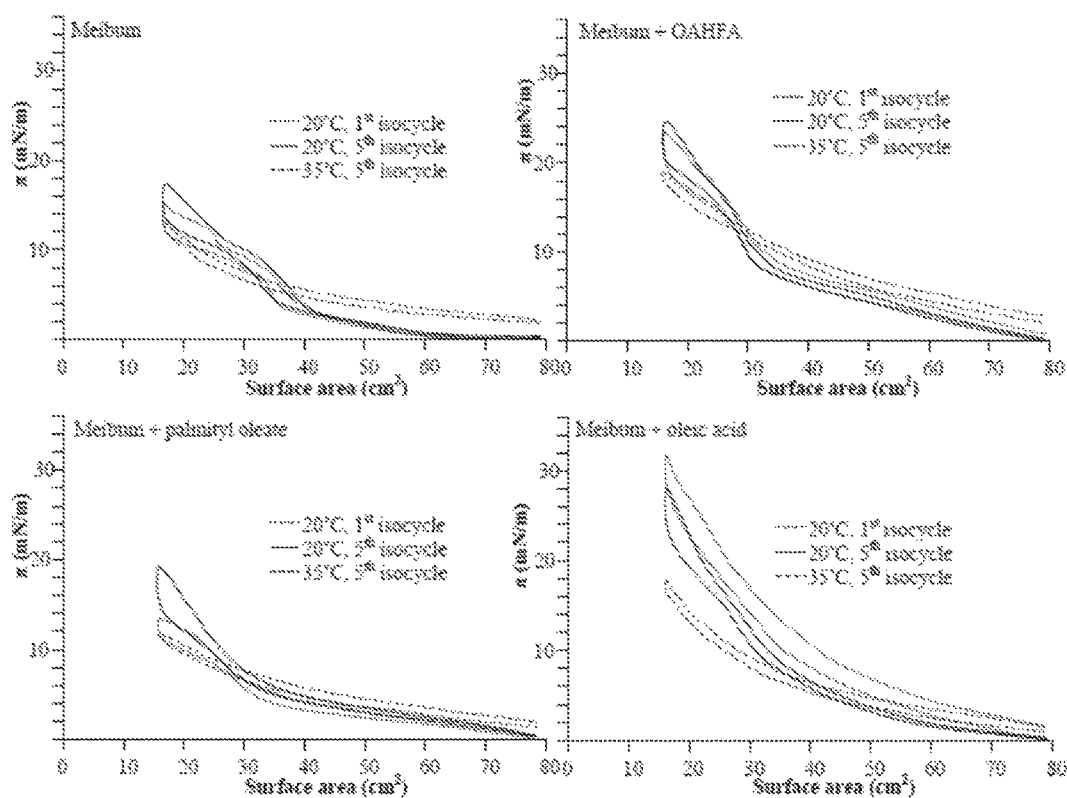
FIG. 5 shows surface pressure/area curves for meibum (20 μg) containing 0.5% (w/w) fluorophore (top left), or meibum (20 μg) containing 0.5% (w/w) fluorophore mixed with 3.7 nmol of C16:0-C18:1 OAHFA (2 μg) (top right), 3.7 nmol palmityl oleate (bottom left), or 3.7 nmol oleic acid (bottom right), showing the first and fifth isocycles at 20° C., and the fifth isocycle after the trough was heated to 35° C.

In general, meibomian films were very tolerant to the changes in their composition, indicated by the fact that the shapes of the different Π-A curves of mixed films were similar to those obtained from films of pure meibomian lipids (FIG. 5). FIG. 5 shows surface pressure/area curves for meibum and meibum mixed with different lipids. Meibum containing fluorophore was spread on artificial tear buffer alone or pre-mixed with each of (O-oleoyl)-ω-hydroxypalmitic acid, palmityl oleate, or oleic acid were spread at 20° C. on the trough. After five isocycles, the trough was heated to 35° C. and five more isocycles were carried out. Then the trough was cooled back to 20° C. and again five more isocycles were run.

$\Pi_{max}$ in the first isocycle after spreading the films at 20° C. was higher in the case of meibum mixed with (O-oleoyl)-ω-hydroxypalmitic acid or oleic acid than for meibomian lipid films alone, whereas palmityl oleate did not influence this (FIG. 5). Subsequent isocycles resulted in a small increase in $\Pi_{max}$ for films of meibomian lipids plus (O-oleoyl)-ω-hydroxypalmitic acid, but there was a marked increase in $\Pi_{max}$ for the films of meibomian lipids plus palmityl oleate. The opposite occurred for films of meibomian lipids plus oleic acid, where $\Pi_{max}$ decreased in subsequent isocycles (FIG. 5). After heating the films, for all mixtures the Π-A curves became smoother and $\Pi_{max}$ decreased, and upon cooling back to 20° C. all mixtures had a higher $\Pi_{max}$ than before heating, but retained the shape of the curve (not shown). This is similar for pure meibomian lipid films.

Figure 6:
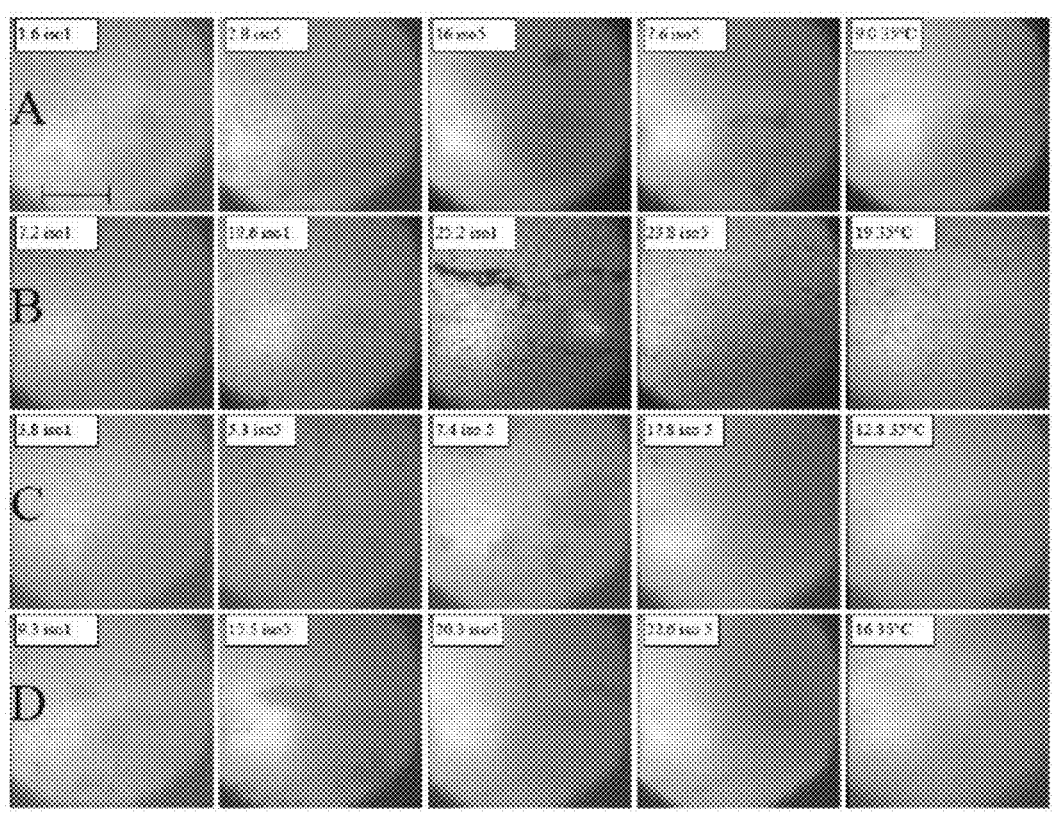
FIG. 6 shows micrographs of meibomian lipid films as of FIG. 5. Micrographs comparing the appearance of pure meibomian lipid films (Row A) with meibomian lipids mixed with the OAHFA (Row B), palmityl oleate (Row C) or oleic acid (Row D) at 20° C. In each box, the surface pressure during compression of the film and the isocycle is given, e.g. 1.6 iso 1 means that the pressure was 1.6 mN/m during compression in isocycle 1. The last column shows the appearance of the films at 35° C. Scale=100 μm.

Microsopically, the appearance of the meibomian films plus (O-oleoyl)-ω-hydroxypalmitic acid was different from the others. In particular, regular dark spots appeared in the films, and at higher pressures there were also streaky dark regions (FIG. 6). FIG. 6 shows micrographs of meibomian lipid films.

Micrographs comparing the appearance of pure meibomian lipid films (Row A) with meibomian lipids mixed with the (O-oleoyl)-ω-hydroxypalmitic acid (Row B), palmityl oleate (Row C) or oleic acid (Row D) at 20° C. In each box, the surface pressure during compression of the film and the isocycle is given, e.g. 1.6 iso 1 means that the pressure was 1.6 mN/m during compression in isocycle 1. The last column shows the appearance of the films at 35° C. These dark regions were all oriented in approximately the same direction, which may indicate that the film was buckling or creasing in these areas (FIG. 6). Although present, the spots were less pronounced after a number of isocycles and it appeared as if the dark spots had merged or had organized differently. At 35° C., the dark spots were present but appeared larger and at higher pressure some dark lines marbling the film could be seen. When cooled back to 20° C., at lower pressures, the film had a relatively even, but mottled, appearance and this mottling was more obvious at higher pressures. Films of meibomian lipids plus either palmityl oleate or oleic acid did not appear substantially different from pure meibomian lipid films (FIG. 6). They showed patchiness at low pressures and these patches decreased in size at higher pressures. Although not quantitatively verified, the darker patches appeared to be more prevalent in the mixed films of palmityl oleate and oleic acid than for pure meibomian lipid films.

6.5 Discussion

Despite their structural similarity to the corresponding wax esters, the data indicates that (O-oleoyl)-ω-hydroxypalmitic acid is much more surface active. The structural nature of (O-oleoyl)-ω-hydroxypalmitic acid indicates that they may be able to serve both as a surfactant and a bridge between polar and non-polar phases.

This surface activity of (O-oleoyl)-ω-hydroxypalmitic acid is most likely a result of both the free acid group (negatively charged at neutral pH) and the polar ester bond. For wax esters, interaction with the aqueous phase is confined to the polar ester group with the acyl chains pushed above the surface to form a V shape. As the molecules are pushed together further, some leave the interface to lie above the interfacial layer into a bulk top layer. This would account for the flattening of the Π-A curve at 25 cm²-28 cm² (FIG. 4) representing an area per molecule of about 60 Å² assuming the film is a monolayer up to this point. These molecules would rearrange to form a stable non-polar phase and hence would not return to the surface. This would also account for the shift in take-off to smaller surface areas in subsequent isocycles. Although it appears as though the same might be occurring for (O-oleoyl)-ω-hydroxypalmitic acid films due to the similar flattening of their Π-A curves, the inventors believe that this is not the case. Instead, without wishing to be bound by theory, it is proposed that the (O-oleoyl)-ω-hydroxypalmitic acid, as an example of a compound of formula (I), initially interacts with the surface strongly with the carboxyl group and weakly at the ester group. Effectively, this means that one of the alkyl chains would be anchored flat on the surface and the other would be free to move above the surface. This feature is consistent with the initial large surface area per molecule compared with the wax ester. As the surface area decreases, the flexible molecules are initially forced into a structure covering less volume. It is speculated, that at a critical pressure the contact of the ester bond at the surface would be lost and the whole molecule would tilt off the aqueous surface, but still remain attached through the carboxyl group. This would be consistent with the flattening of the Π-A curve during compression and is also supported if one estimates the surface area per molecule on take-off: 82 Å² per molecule, for palmityl oleate films, and 131 Å² per molecule for a (O-oleoyl)-ω-hydroxypalmitic acid film. At still smaller surface areas, the (O-oleoyl)-ω-hydroxypalmitic acid film Π-A profile again becomes steeper, which is consistent with the (O-oleoyl)-ω-hydroxypalmitic acid molecules being attached to the surface at their carboxyl group and being compressed laterally, tilting the molecules vertically upwards relative to the surface. In any case, this feature of the (O-oleoyl)-ω-hydroxypalmitic acid derived films and the ability to take up a normal (right angle) orientation from the surface would give these molecules the capacity to form a bridge between the aqueous and outer bulk layer.

Surface Properties of Meibomian Lipid Films Mixed with Other Lipids

There was a marked similarity in appearance of the films seeded with palmityl oleate and oleic acid and meibomian lipid films alone; there were no obvious structural changes that corresponded to the increase in $\Pi_{max}$ for the palmityl oleate mixed film or for the decrease in $\Pi_{max}$ for the oleic acid mixed film during the course of a number of isocycles. In contrast, there was a marked structural change to the films containing (O-oleoyl)-ω-hydroxypalmitic acid. The regularity of the size and spacing of the dark spots is reminiscent of liquid condensed phases reported in films of dipalmityl phosphate (Hiranita H, Nakamura S, Kawachi M, Courrier H M, Vandamme T F, Krafft M P, Shibata O, 2003, "Miscibility behavior of dipalmitoylphosphatidylcholine with a single-chain partially fluorinated amphiphile in Langmuir monolayers", *J. Coll. Inter. Sci.* 265:83-92). Also striking of the films containing the (O-oleoyl)-ω-hydroxypalmitic acid was a more even and homogenous appearance of these films compared with the other films. This could be due to the interaction of the surfactant with both the surface and the bulk hydrophobic phase. This would imply the absence of discretely definable layers in the film. Such an idea is indeed supported by the inventors' own observations that thinly spread meibum in its liquid expanded phase can be seen as a polar surfactant layer with a thickness of several molecules in length (5 nm) which is possibly made from (O-acyl)-ω-hydroxy fatty acid already mixed with significant amounts of non-polar component of the meibum, like cholesterol esters and wax esters. Since multilayered film structures based on non-polar molecules on top of a polar surface are energetically unstable and tend to form aggregates like lenses and droplets, one function of the compound of formula (I) (of which (O-oleoyl)-ω-hydroxypalmitic acid is a member) could be to stabilise this multilayered arrangement found for meibomian films and tears.

In conclusion, the data in this Example is consistent with compounds of formula (I) helping the meibomian film to maintain a balance between polar and non-polar layers of the TFLL, which in turn helps to stabilise/buffer the system during spreading and pressure stress such as blinking. Thus, compounds of formula (I) could be used in an artificial tear formulation to stabilize the disrupted tear film of patients suffering from dry eye and related ailments.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. An ophthalmic formulation for effectively treating dry eye in a subject in need thereof, comprising therapeutically effective amounts of a compound of formula (I):

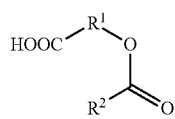
(I)

wherein

R$^1$ is a linear or branched C$_9$-C$_{33}$ alkyl or a linear or branched C$_9$-C$_{17}$ alkenyl with 1, 2, or 3 double bonds;

R$^2$ is a linear or branched C$_9$-C$_{19}$ alkyl or a linear or branched C$_9$-C$_{19}$ alkenyl with 1 to 4 double bonds;

and an ophthalmologically acceptable carrier, wherein the ophthalmic formulation is an oil-in-water emulsion, ointment, or gel.

2. An ophthalmic formulation according to claim 1, wherein HOOC—R$^1$— is selected from the group consisting of: capryl (C10:0), lauryl (C12:0), myristyl (C14:0), palmityl (C16:0), stearyl (C18:0), oleoyl (C18:1), linoleoyl (w6) (C18:2), and linoleoyl (ω3) (C18:3).

3. An ophthalmic formulation of claim 1, wherein R$^2$ is linear or branched C$_{17}$ alkyl or linear or branched C$_{17}$ alkenyl with 1 or 2 double bonds.

4. An ophthalmic formulation of claim 1, wherein R$^2$ is linear or branched C$_{19}$ alkenyl with 4 double bonds.

5. An ophthalmic formulation of claim 1, wherein the compound of formula (I) is selected from the group consisting of:

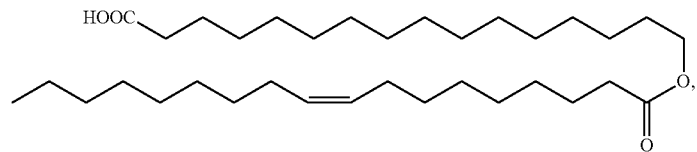 [SMILES: CCCCCCCC/C=C\CCCCCCCC(=O)OCCCCCCCCCCCCCCCC(=O)O]

(O-oleoyl)-16-hydroxypalmitic acid (C16:0-C18:1):

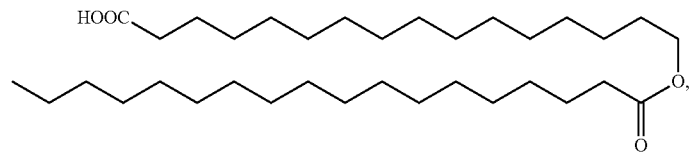

(O-stearyl)-16-hydroxypalmitic acid (C16:0-C18:0):

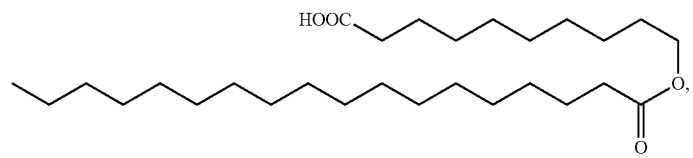

(O-stearyl)-10-hydroxycaprinic acid (C10:0-C18:0):

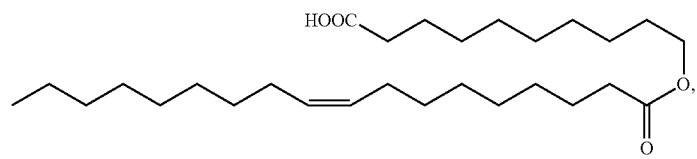 [SMILES: CCCCCCCC/C=C\CCCCCCCC(=O)OCCCCCCCCCC(=O)O]

(O-oleoyl)-10-hydroxycaprinic acid (C10:0-C18:1):

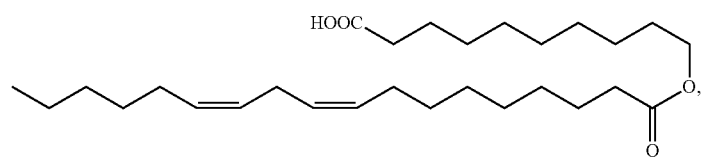

(O-linoleoyl)-10-hydroxycaprinic acid (C10:0-C18:2):

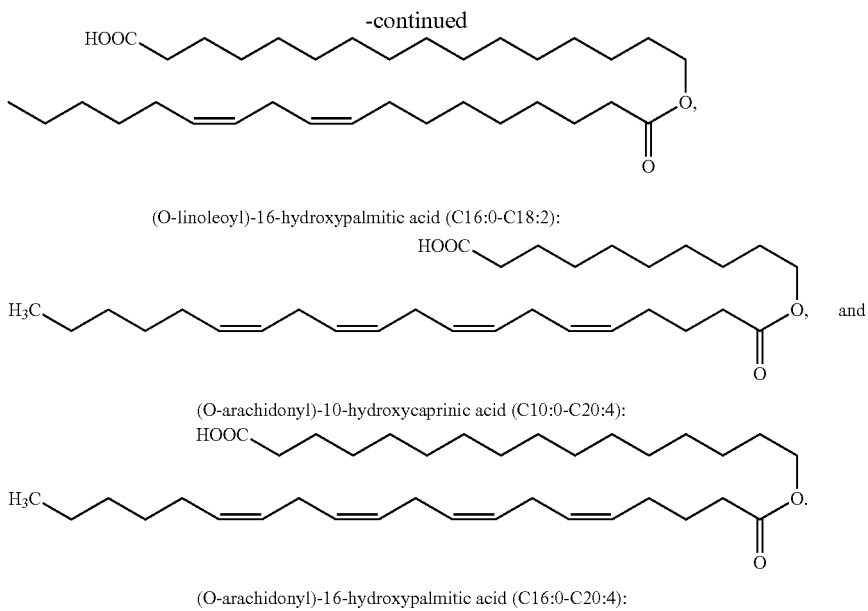

(O-linoleoyl)-16-hydroxypalmitic acid (C16:0-C18:2):

(O-arachidonyl)-10-hydroxycaprinic acid (C10:0-C20:4):

(O-arachidonyl)-16-hydroxypalmitic acid (C16:0-C20:4):

6. An ophthalmic formulation according to claim 1, wherein the compound of formula (I) is (O-oleoyl)-16-hydroxypalmitic acid.

7. An ophthalmic formulation according to claim 1, wherein the ophthalmologically acceptable carrier is, or comprises, water.

8. An ophthalmic formulation of claim 1, wherein the ophthalmic formulation further comprises an ophthalmologically acceptable excipient.

9. An ophthalmic formulation according to claim 8, wherein the ophthalmologically acceptable excipient is selected from the group consisting of demulcents, emollients, hypertonicity agents, preservatives, buffers and pH adjusting agents.

10. An ophthalmic formulation of claim 1, wherein the ophthalmic formulation is an oil-in-water emulsion.

11. An ophthalmic formulation of claim 1, wherein the ophthalmic formulation comprises liposomes.

12. An ophthalmic formulation comprising a compound of formula (I) as defined in claim 1, water, and an emulsifying agent.

13. An ophthalmic formulation comprising a compound of formula (I) as defined in claim 1, water, and one or more ophthalmologically acceptable excipients selected from the group consisting of polyethylene glycol, propylene glycol, glycerin, polyvinyl alcohol, povidone, polysorbate 80, hydroxypropyl methylcellulose, carmellose, carbomer 980, sodium hyaluronate and dextran.

14. An ophthalmic formulation of claim 1, further comprising an active pharmaceutical ingredient for treating a condition or disease of the eye.

15. A method for the treatment of dry eye comprising topically administering to the eye of a subject in need thereof a therapeutically effective amount of an ophthalmic formulation of claim 1.

16. A compound selected from the group consisting of:

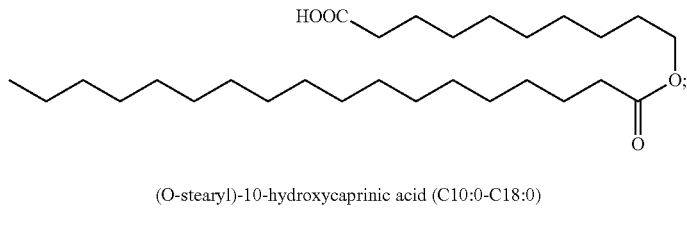

(O-stearyl)-10-hydroxycaprinic acid (C10:0-C18:0)

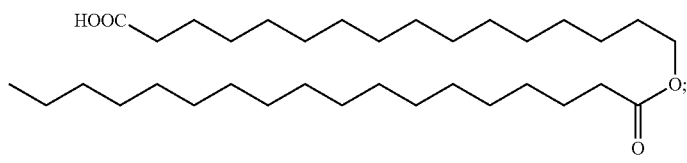

(O-stearyl)-16-hydroxypalmitic acid (C16:0-C18:0)

-continued

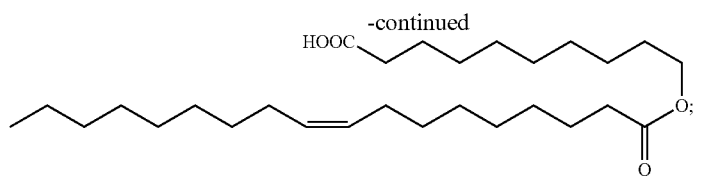

(O-oleoyl)-10-hydroxycaprinic acid (C10:0-C18:1)

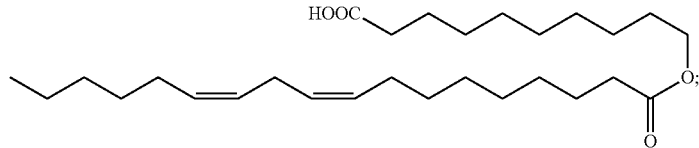

(O-linoleoyl)-10-hydroxycaprinic acid (C10:0-C18:2)

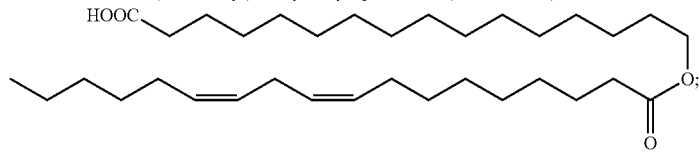

(O-linoleoyl)-16-hydroxypalmitic acid (C16:0-C18:2)

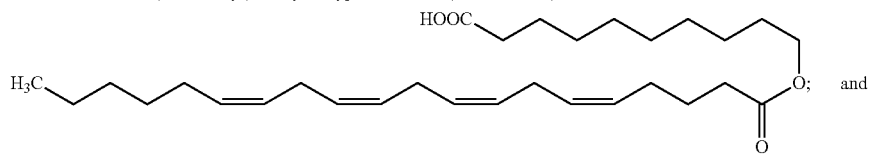

(O-arachidonyl)-10-hydroxycaprinic acid (C10:0-C20:4)

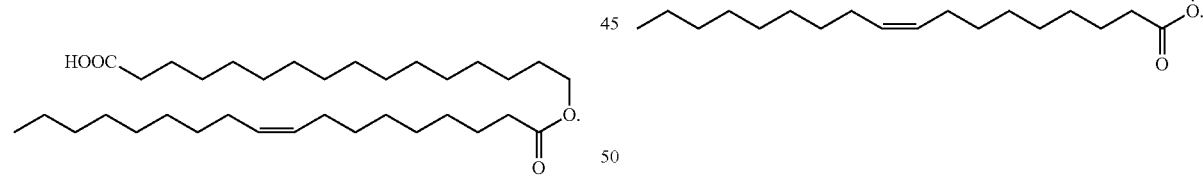

(O-arachidonyl)-16-hydroxypalmitic acid (C16:0-C20:4)

17. An ophthalmic formulation of claim 5, wherein the compound of formula (I) is (O-oleoyl)-16-hydroxypalmitic acid (C16:0-C18:1):

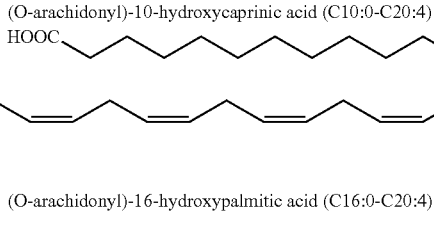

18. An ophthalmic formulation of claim 5, wherein the compound of formula (I) is (O-oleoyl)-10-hydroxycaprinic acid (C10:0-C18:1):

19. An ophthalmic formulation according to claim 1, wherein the compound of formula (I) is present in an amount ranging from about 0.001 wt % to about 20 wt %.

* * * * *